United States Patent
Shepherd

(10) Patent No.: US 11,905,532 B2
(45) Date of Patent: Feb. 20, 2024

(54) COMPOSITIONS AND METHODS FOR MOLECULAR MEMORY STORAGE AND RETRIEVAL

(71) Applicant: Massachusetts Institute of Technology, Cambridge, MA (US)

(72) Inventor: Tyson Robert Shepherd, Louisville, CO (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 606 days.

(21) Appl. No.: 16/912,458

(22) Filed: Jun. 25, 2020

(65) Prior Publication Data

US 2020/0407697 A1 Dec. 31, 2020

Related U.S. Application Data

(60) Provisional application No. 62/866,571, filed on Jun. 25, 2019.

(51) Int. Cl.
   *C12N 7/00* (2006.01)
   *C12N 15/70* (2006.01)
   (Continued)

(52) U.S. Cl.
   CPC .............. *C12N 7/00* (2013.01); *B01L 3/5085* (2013.01); *C12N 15/1037* (2013.01);
   (Continued)

(58) Field of Classification Search
   CPC ...... C12N 7/00; C12N 15/1037; C12N 15/70; C12N 2795/14121; C12N 2795/14152; B01L 3/5085; C12Q 1/6874
   See application file for complete search history.

(56) References Cited

U.S. PATENT DOCUMENTS

| 4,816,567 A | 3/1989 | Cabilly |
| 5,356,802 A | 10/1994 | Chandrasegan |

(Continued)

FOREIGN PATENT DOCUMENTS

| CN | 106119269 | 11/2016 |
| WO | 98/53059 | 11/1998 |

(Continued)

OTHER PUBLICATIONS

Abramoff, et al., "Multiple sclerosis in children", *Biophotonics Int.*, 11(2):36-42 (2004).

(Continued)

*Primary Examiner* — Brian J. Sines
(74) *Attorney, Agent, or Firm* — PABST PATENT GROUP LLP

(57) ABSTRACT

Compositions and methods for the storage, organization, access, and retrieval of information encoded by sequence controlled polymers such as data storage nucleic acids are provided. In some embodiments, organization, storage, and/or selective retrieval of the data is facilitated by hybridization of barcode sequence of the sequence controlled polymer to the reverse complementary sequence of an oligonucleotide. The plurality of oligonucleotides can be arrayed using a known organization scheme, and selectively capture and localize the corresponding sequence controlled polymer. In some embodiments, the compositions and methods utilize recombinant bacteriophage, typically featuring a minigenome having a bacteriophage origin of replication and packaging signal separated from a data storage sequence by barcodes.

29 Claims, 8 Drawing Sheets

(51) Int. Cl.
    *C12N 15/10*     (2006.01)
    *C12Q 1/6874*    (2018.01)
    *B01L 3/00*      (2006.01)

(52) U.S. Cl.
    CPC .......... *C12N 15/70* (2013.01); *C12Q 1/6874* (2013.01); *B01L 2200/16* (2013.01); *B01L 2300/0829* (2013.01); *C12N 2795/14121* (2013.01); *C12N 2795/14152* (2013.01)

(56) References Cited

U.S. PATENT DOCUMENTS

| | | | |
|---|---|---|---|
| 5,436,150 | A | 7/1995 | Chandrasegan |
| 5,487,994 | A | 1/1996 | Chandrasegan |
| 5,624,821 | A | 4/1997 | Winter |
| 6,140,081 | A | 10/2000 | Barbas |
| 6,194,551 | B1 | 2/2001 | Idusogie |
| 6,453,242 | B1 | 9/2002 | Eisenberg |
| 6,534,261 | B1 | 3/2003 | Cox |
| 6,610,512 | B1 | 8/2003 | Barbas |
| 6,746,838 | B1 | 6/2004 | Choo |
| 6,866,997 | B1 | 3/2005 | Choo |
| 7,067,617 | B2 | 6/2006 | Barbas |
| 8,227,242 | B2 | 7/2012 | Bradbury |
| 8,501,923 | B2 | 8/2013 | Rothemund |
| 2002/0165356 | A1 | 11/2002 | Barbas |
| 2003/0215914 | A1 | 11/2003 | Houtager |
| 2004/0180422 | A1 | 9/2004 | Hoet |
| 2004/0197892 | A1 | 10/2004 | Moore |
| 2005/0147962 | A1 | 7/2005 | Wagstrom |
| 2007/0117109 | A1 | 5/2007 | Rothemund |
| 2007/0128728 | A1 | 6/2007 | Bradbury |
| 2007/0154989 | A1 | 7/2007 | Barbas |
| 2007/0213269 | A1 | 9/2007 | Barbas |
| 2012/0251583 | A1 | 10/2012 | Rothemund |
| 2013/0295614 | A1 | 11/2013 | Hareendran |
| 2018/0141020 | A1* | 5/2018 | Gunderson .......... B01J 19/0046 |
| 2019/0142882 | A1* | 5/2019 | Shepherd ............. C07K 14/005 536/23.1 |
| 2019/0203242 | A1 | 7/2019 | Praetorius |
| 2020/0181602 | A1 | 6/2020 | Zobeck |

FOREIGN PATENT DOCUMENTS

| | | |
|---|---|---|
| WO | 9853059 | 11/1998 |
| WO | 99/58572 | 11/1999 |
| WO | 9958572 | 11/1999 |
| WO | 2000/071694 | 11/2000 |
| WO | 2000071694 | 11/2000 |
| WO | 2003/016496 | 2/2003 |
| WO | 2003016496 | 2/2003 |
| WO | 2004/048543 | 6/2004 |
| WO | 2004048543 | 6/2004 |
| WO | 2007/067818 | 6/2007 |
| WO | 2007067818 | 6/2007 |
| WO | 2013/176772 | 11/2013 |
| WO | 2013176772 | 11/2013 |
| WO | 2014/018423 | 6/2014 |
| WO | 2014018423 | 6/2014 |
| WO | 2017/089567 | 6/2017 |
| WO | 2017/089570 | 6/2017 |
| WO | 2017089567 | 6/2017 |
| WO | 2017089570 | 6/2017 |
| WO | 2017/189870 | 11/2017 |
| WO | 2017/189914 | 11/2017 |
| WO | 2017189870 | 11/2017 |
| WO | 2017189914 | 11/2017 |
| WO | 2019/094928 | 5/2019 |
| WO | 2019094928 | 5/2019 |
| WO | 2020/051507 | 3/2020 |
| WO | 2020051507 | 3/2020 |

OTHER PUBLICATIONS

Ailenberg, et al., "An improved Huffman coding method for archiving text, images, and music characters in DNA", *BioTechniques.*, 47(3):747-754 (2009).

Amunts, et al., "Ribosome. The structure of the human mitochondrial ribosome", *Science.*, 348(6230):95-98 (2015).

Angal, et al., "A single amino acid substitution abolishes the heterogeneity of chimeric mouse/human (IgG4) antibody", *Mol. Immunol.*, 30(1):105-08 (1993).

Anonymous, et al., "M13mp18 (Cloning Vector)", *New England BioLabs Catalog*, http://international.neb.com/-/media/nebus/page-images/tools/dna-sequences-and-maps/m13mp18_map.pdf?la=en&hash+ABF432A1085CFA7CA7850D00B69ACBE654DFC580 (2002).

Arita, et al., "Chapter 368: DNA Memory", *Handbook of Natural Compu*, 1281-1318 (2012).

Arizona State University, "Top-down design brings new DNA structures to life", retrieved from the internet: URL:https://phys.org/news/2016-05-top-down-dna-life.html:1-4 (2016).

Babaei, "A novel text and image encryption method based on chaos theory and DNA computing", *Nat Comput.*, 12:101-107 (2013).

Bai, et al., "Cryo-EM structure of a 3D DNA-origami object", *Proc. Natl. Acad. Sci.* 109(49):20012-20017 (2012).

Banal, et al., "Random access DNA memory in a scalable, archival file storage system", *bioRxiv*, 1-29 (2020).

Bee, et al., "Content-Based Similarity Search in Large-Scale DNA Data Storage Systems", *bioRxiv*, 1-19 (2020).

Benson, et al., "DNA rendering of polyhedral meshes at the nanoscale", *Nature*, 523(7561):441-444 (2015).

Benson, et al., "Computer-Aided Production of Scaffolded DNA Nanostructures from Flat Sheet Meshes", *Angewandte Chemie*, 55(31):8869-8872 (2016).

Benson, et al., "Supplementary Material for DNA rendering of polyhedral meshes at the nanoscale", *Nature*, 523(7561):441-444 (2015).

Bent, et al., "On non-intersecting Eulerian circuits", *Discrete Appl. Math.* 18(1):87-94 (1987).

Bhatia, et al., "Icosahedral DNA nanocapsules by modular assembly", *Angew. Chem. Int. Ed.*, 48(23):4134-4137 (2009).

Bornholt, et al., "A DNA-based Archival Storage System", *21th ACM International Conference on Architectural Support for Programming Languages and Operating Systems*, 1-13, (2016).

Braasch, et al., "Locked nucleic acid (LNA): Fine-tuning the recognition of DNA and RNA", *Chem. Biol.*, 8(1):1-7 (2001).

Brown, et al., "An easy-to-prepare mini-scaffold for DNA origami", *Nanoscale*, 7(40):16621-4 (2015).

Brudno, et al., "Recent progress toward the templated synthesis and directed evolution of sequence-defined synthetic polymers", *Chem. Biol.*, 16(3):265-276 (2009).

Castro, et al., "A primer to scaffolded DNA origami", *Nat. Methods.*, 8(3):221-229 (2011).

Chandran, et al., "DNA origami: Folding DNA into Desired Shapes", *Fourth Warft Workshop on Brain Modeling and Supercomputing*, (2009).

Chasteen, et al., Eliminating helper phage from phage display Nucleic Acids Res., 34(21):e145 (2006).

Cho, et al., "An unnatural biopolymer", *Science*, 261(5126):1303-1305 (1993).

Church, et al. "Next-generation digital information storage in DNA", *Science*, 337(6102):1628 (2012).

Clelland, et al., "Hiding messages in DNA microdots", *Nature*, 399(673):533-534 (1999).

Cong, "Multiplex genome engineering using CRISPR/Cas systems",*Science*, 15:339(6121):819-823 (2013).

Cui, et al., "An encryption scheme using DNA technology", *2008 Third International Conference on Bio-Inspired Computing: Theories and Applications.*, 37-41(2008).

Dietz, et al., "Folding DNA into twisted and curved nanoscale shapes", *Science*, 325(5941):725-730 (2009).

Dotto, et al., "Initiation and termination of phage f1 plus-strand synthesis", *Proc. Natl. Acad. Sci. U.S.A.*, 79(23):7122-7126 (1982).

Douglas, et al., "A logic-gated nanorobot for targeted transport of molecular payloads", *Science*, 335(6070):831-834 (2012).

(56) References Cited

OTHER PUBLICATIONS

Douglas, et al., "Rapid prototyping of 3D DNA-origami shapes with caDNAno", *Nucleic Acids Res.*, 37(15):5001-5006 (2009B).
Douglas, et al., "Self-assembly of DNA into nanoscale three-dimensional shapes", *Nature*, 459(7245):414-418 (2009A).
Dunn, et al., "Guiding the folding pathway of DNA origami", *Nature*, 525(7567):82-86 (2015).
Dutta, et al., "DNA-directed artificial light-harvesting antenna", *Journal of the American Chemical Society*, 133(31):11985-11993 (2011).
Elbashir, et al., "Duplexes of 21-nucleotide RNAs mediate RNA interference in cultured mammalian cells", *Nature*, 411(6836):494-498 (2001).
Elbaz, et al., "Genetic encoding of DNA nanostructures and their self-assembly in living bacteria", *Nat Commun*, 7:11179 (2016).
Ellis-Monaghan, et al., "DNA origami and the complexity of Eulerian circuits with turning costs", *Nat. Comput.*, 14(3):491-503 (2015).
Ennifar, et al., "Targeting the dimerization initiation site of HIV-1 RNA with aminoglyocosides: from crystal to cell", *Nucleic Acids Research.*, 34(8):2328-2339 (2006).
Faber, et al., "Structural Rearrangements of HIV-1 Tat-responsive RNA upon Binding of Neomycin B*", *The Journal of Biological Chemistry*. 275(27):20660-20666 (2000).
Fan, et al., "Gating machinery of InsP3R channels revealed by electron cryomicroscopy", *Nature*, 527(7578):336-341 (2015).
Fang, et al., "An unusual Toplogical Structure of the HIV-1 Rev Response Element", *Cell*, 155(3):594-605 (2013).
Fang, et al., "Small-angle X-ray scattering: a bridge between RNA secondary structures and three-dimensional topological structures", *Current Opinion in Structural Biology*, 30:147-160 (2015).
Fire, et al. "Potent and specific genetic interference by double-stranded RNA in Caenorhabditis elegans", *Nature*, 391(6669):806-11 (1998).
Fu, et al., "DNA double-crossover molecules", *Biochemistry*, 32(13):3211-3220 (1993).
Fu, et al., "Controlled drug release by a nanorobot", *Nature Biotechnology*, 30(5):407-408 (2012).
Geary, et al., "RNA nanostructures. A single-stranded architecture for cotranscriptional folding of RNA nanostructures", *Science*, 345(6189):799-804 (2014).
Gehani, et al., "DNA-based Cryptography", *Lect Notes Comput Sc.*, 2950:167-188 (2004).
Gellman, "Foldamers: A Manifesto", *Acc. Chem. Res.*, 31(4):173-180 (1998).
Goldman et al., "Towards practical, high-capacity, low-maintenance information storage in synthesized DNA", *Nature*, 494(7435):77-80 (2013).
Gradišar, et al., "Design of a single-chain polypeptide tetrahedron assembled from coiled-coil segments", *Nat. Chem. Biol.*, 9(6):362-366 (2013).
Grass, et al., "Robust chemical preservation of digital information on DNA in silica with error-correcting codes", *Angew. Chem. Int. Ed.*, 54(8):2552-2555 (2015).
Gruber, et al., "Efficient tumor cell lysis mediated by a bispecific single chain antibody expressed in *Escherichia coli*.", *J. Immunol.*, 152(11):5368 (1994).
Gu, et al., "Dynamic patterning programmed by DNA tiles captured on a DNA origami substrate", *Nature Nanotechnology*, 4(4):245-248 (2009).
Han, et al., "DNA gridiron nanostructures based on four-arm junctions", *Science*. 339(6126):1412-1415 (2013).
Han, et al., "DNA origami with complex curvatures in three-dimensional space", *Science*, 332(6027):342-346 (2011).
Han, et al., "Single-stranded DNA and RNA origami", *Science*, 358(6369) (2017).
Hannon, "RNA interference", *Nature*, 418(6894):244-251 (2002).
He, et al., "Hierarchical self-assembly of DNA into symmetric supramolecular polyhedra", *Nature*, 452(7184):198-201 (2008).
He, et al., "On the Chirality of Self-Assembled DNA Octahedra", *Angew. Chem.*, 122(4):760-763 (2010).
Henderson, et al., "Outcome of the first electron microscopy validation task force meeting", *Structure*, 20(2):205-214 (2012).
Hollinger, et al., "Diabodies: small bivalent and bispecific antibody fragments", *Proc. Natl. Acad. Sci. U.S.A.*, 90(14):6444-6448 (1993).
Howe, et al., "Seletive small-molecule inhibition of an RNA structural element", *Nature*, 526(7575):672-677 (2015).
Iinuma, et al., "Polyhedra Self-Assembled from DNA-PAINT", *Science*, 344(6179): 65-69 (2014).
Iinuma et al., "Supplementary Material for Polyhedra self-assembled from tripods and Characterized with 3D DNA-PAINT", *Science*, 344(6179):65-69 (2014).
Irobalieva, et al., "Structural diversity of supercoiled DNA", *Nat. Commun.*, 6:8440 (2015).
Jiang, et al., "DNA origami as a carrier for circumvention of drug resistance", *Journal of the American Chemical Society*, 134(32):13396-13403 (2012).
Jinek, et al., "A programmable dual-RNA-guided DNA endonuclease in adaptive bacterial immunity", *Science*, 337(6096):816-21 (2012).
Jones, et al., "Small-angle X-ray scattering-derived structure of the HIV-1 5' UTR reveals 3D tRNA mimicry", Proceedings of the National Academy of Sciences of the United States of America, 111(9):3395-3400 (2014).
Jones, et al., "Nanomaterials. Programmable materials and the nature of the DNA bond", *Science*, 347(6224):1260901 (2015).
Kallenbach, et al., "An immobile nucleic acid junction constructed from oligonucleotides", *Nature*, 305:829-831 (1983).
Kazantsev, et al., "High-resolution structure of RNase P protein from *Thermotoga maritima*", Proceedings of the National Academy of Sciences of the United States of America, 100(13): 7497-7502 (2003).
Ke, et al. "Multilayer DNA Origami Packed on a Square Lattice", *J. A. Chem. Soc.*, 131(43):15903-15908 (2009).
Ke, et al., "DNA brick crystals with prescribed depths", *Nat. Chem.*, 6(11):994-1002 (2014).
Ke, et al., "Three-dimensional structures self-assembled from DNA bricks", *Science*, 338(6111):1177-1183 (2012A).
Ke, et al., "Two design strategies for enhancement of multilayer-DNA-origami folding: underwinding for specific intercalator rescue and staple-break positioning", *Chem. Sci.*, 3(8):2587-2957 (2012B).
Ke, et al., "Self-Asssembled Water-Soluble Nucleic Acid Probe Tiles for Label-Free RNA Hyrbidization Assays", *Science*, 319(5860):180-183 (2008).
Keane, et al., "Structure of the HIV-1 RNA packaging signal", *Science*, 348(6237):917-921 (2015).
Kertesz, et al., "Genome-wide measurement of RNA secondary structure in yeast", *Nature*, 467(7311):103-107 (2010).
Kick, et al., "Efficient Production of Single-Stranded Phage DNA as Scaffolds for DNA Origami", *Nano Lett*, 15(7):4672-6 (2015).
Kim, et al., "Extending lifetime of flash memory using strong error correction coding", *IEEE Trans. Consum. Electron.*, 61:206-214 (2015).
Kim, et al. "Insertion and deletion mutants of FokI restriction endonuclease", *J. Biol. Chem.*, 269(50):31978-31982 (1994B).
Kim, et al., "Chimeric restriction endonuclease", *Proc. Natl. Acad. Sci. USA.*, 91(3):883-887 (1994A).
Kim, et al., "Electrowetting on dielectric (EWOD) properties of Teflon-coated electrosprayed silica layers in air and oil media and the influence of electric leakage", *J. Mater. Chem. C*, 6(42):6808-6815 (2018).
Ko, et al., "Synergistic self-assembly of RNA and DNA molecules", *Nature Chemistry*, 2(12):1050-1055 (2010).
Kostelny, et al., "Formation of a bispecific antibody by the use of leucine zippers", *J. Immunol.*, 148(5):1547-1553 (1992).
Krishnan, et al., "Designer nucleic acids to probe and program the cell", *Trends in Cell Biology*, 22(12):624-633 (2012).
Kuang, et al., "Nanoscale Superstructures Assembled by Polymerase Chain Reaction (PCR): Programmable Construction, Structural Diversity, and Emerging Applications", Accounts of Chemical Research, 46(11):2341-2354 (2013).
Kurreck, et al., "Design of antisense oligonucleotides stabilized by locked nucleic acids", *Nucleic Acids Res.*, 30(9):1911-1918 (2002).

(56) References Cited

OTHER PUBLICATIONS

Kuzyk, et al., "DNA-Based Self-Assembly Of Chiral Plasmonic Nanostructures With Tailored Optical Response", *Nature*, 483(7389):311-314 (2012).
Ledsgaard, et al., "Basics of Antibody Phage Display Technology," *Toxins*, 10(236), 15 pages (2018).
Leier, et al., "Cryptography with DNA binary strands", *Biosystems*, 57(1):13-22 (2000).
Li, et al., "Alteration of the cleavage distance of Fok I restriction endonuclease by insertion mutagenesis", *Proc. Natl. Acad. Sci. USA*, 90(7):2764-2768 (1993).
Li, et al., "Functional domains in Fok I restriction endonuclease", *Proc., Natl. Acad. Sci. USA*, 89(10):4275-4279 (1992).
Li, et al., "Nucleic-based nanoengineering: novel structures for biomedical applications", *Interface Focus*, 1(5): 702-724 (2011).
Li, et al., "Quantifying Absolute Protein Synthesis Rates Reveals Principles Underlying Allocation of Cellular Resources", *Cell*, 157(3):624-635 (2014).
Li, et al., "Engineering neucleic acid structures for programmable molecular circuitry and intracellular biocomputation", *Nature Chemistry*, 9(11):1056-1067 (2017).
Liedl, et al., "Self-assembly of 3D prestressed tensegrity structures from DNA", Nature Nanotechnology, *Nature Nanotechnology*, 5(7):520-524 (2010).
Lin, et al., "Dynamic and scalable DNA-based information storage", *Nature Communications*, 11(1):2981 (2020).
Linko, et al., "Automated design of DNA origami", *Nature Biotechnology*, 34(8):826-827 (2016).
Liu, et al., "Crystalline two-dimensional DNA-origami array", *Angew Chem Int. Ed*, 50(1):264-7 (2011).
Liu, et al., "Diamond family of nanoparticle superlattices", *Science*, 351(6273):582-586 (2016).
Liu et al., "A DNA Nanostructure Platform for Directed Assembly of Synthetic Vaccines", *Nano Letters*, 12(8):4254-4259 (2012).
Lutz, et al., "Sequence-controlled Polymers", *Science*, 341(6146): 1238149 (2013).
Marchi, et al., "Toward larger DNA origami", *Nano Lett*, 14(10):5740-7 (2014).
Martin, et al., "Magnesium-free self-assembly of multi-layer DNA objects", *Nat. Commun.*, 3:1103 (2012).
Masanori, et al., "Chapter 368: DNA Memory", Handbook of Natural Compu., 1281-1318 (2012).
Maxam et al., "A new method for sequencing DNA", *Proc. Nat. Acad. Sci. USA*, 74(2):560-564 (1977).
Mercer, et al., "Structure and function of long noncoding RNAs in epigenetic regulation", *Nature Structural & Molecular Biology*, 20(3):300-307 (2013).
Michelotti, et al., "Beyond DNA origami: A look on the bright future of nucleic acid nanotechnology", *Wiley Interdiscip Rev Nanomed Nanobiotechnol.*, 4(2):139-152 (2012).
Morrison, et al., "Chimeric human antibody molecules: mouse antigen-binding domains with human constant region domains", *Proc. Natl. Acad. Sci. USA*, 81:6851-6855 (1984).
Nafisi, et al., "Construction of a novel phagemid to produce custom DNA origami scaffolds", *Synthetic Biology*, 3(1):ysy015:1-8 (2018).
Napoli, et al., Introduction of a Chimeric Chalcone Synthase Gene into Petunia Results in Reversible Co-Suppression of Homologous Genes in trans., *Plant Cell*, 2(4):279-289 (1990).
Nayak, et al., "Cas9-mediated genome editing in the methanogenic archaeon Methanosarcina acetivorans", *PNAS*, 114(11) 2976-2981 (2017).
Nelson et al., "Droplet Actuation by Electrowetting-on-Dielectric (EWOD): A Review", *Journal of Adhesion Science and Technology*, 26:747-1771 (2012).
New England Biolabs: Catalog #N4018S, 8 pages (2007).
New England Biolabs: Catalog #N4040S, 13 pages (2007).
Nickels, et al., "DNA origami structures directly assembled from intact bacteriophages", *Small*, 10(9):1765-9 (2014).

Nielsen, et al., "Sequence-selective recognition of DNA by strand displacement with a thymine-substituted polyamide" *Science*, 254(5037):1497-1500 (1991).
Nogales, et al., "Cryo-EM: A Uniquw Tool for the vizualization of Macromolecular Complexity", *Molecular Cell*, 58(4):677-689 (2015).
Norton, et al., "Templates for sequential Assembly of DNA Based Nanostructures", Proceedings of 2005 5th IEEE Conference on Nanotechnology, 3 pages (2005).
Olson, et al., "New Structue Sheds Light on Selective HIV-1 Genomic RNA Packaging", *Viruses*, 7(8):4826-4835 (2015).
Pan, et al., "Lattice-free prediction of three-dimensional structure of programmed DNA assemblies", *Nature Communications.*, 5:5578 (2014A).
Pan, et al., "Structure-based model for light-harvesting properties of nucleic acid nanostructures", *Nucleic Acids Research*, 42(4):2159-2170 (2014B).
Pandey, et al., "Algorithmic design of self-folding polyhedral", *Proc. Natl. Acad. Sci.* 108(50):19885-19890 (2011).
Pardee, et al., "Paper-based synthetic gene networks", *Cell*, 159(4):940-954 (2015).
PartBBa_K1445000, Registry of Standard Biological Parts, Group: iGEM14_CU-Boulder (2014).
Pasqualini, et al., "Organ targeting in vivo using phage display peptide libraries", *Nature*, 380(6572):364-366 (1996).
Peng, et al., "Bottom-up nanofabrication using DNA nanostructures", *Chem Matter*, 28(4):1012-1021 (2016).
Perrault and Shih, "Virus-inspired membrane encapsulation of DNA nanostructures to achieve in vivo stability," *ACS Nano*, 8(5):5132-5140 (2014).
Praetorius, et al., "Biotechnological mass production of DNA origami", *Nature*, 552(7683):84-7 (2017).
Prim, "Shortest connection networks and some generalizations", *Bell Syst. Tech. J.*, 36(6):1389-1401 (1957).
Rashid, et al., "The strategies of DNA immobilization and hybridization detection mechanism in the construction of electrochemical DNA sensor: A review," Sensing and Bio-Sensing Research vol. 16, pp. 19-31, doi:10.1016/j.sbsr.2017.09.001 (2017).
Rhoads, et al., "PacBio Sequencing and its Applications", *Genomics, Proteomics and Bioinformatics*, 13(5):278-289 (2015).
Rich, "The rise of single-molecule DNA biochemistry", *Proc. Natl. Acad. Sci. U. S. A.*, 95(24):13999-14000 (1998).
Rothemund, "Folding DNA to create nanoscale shapes and patterns", *Nature*, 440(7082):297-302 (2006a).
Rothemund, "Scaffolded DNA Origami: from Generalized Multicrossovers to Polygonal Networks", *Nanotechnology: Science and Computation*, 3-21 (2006b).
Rothemund, et al., "Algorithmic self-assembly of DNA Sierpinski triangles", *PLoS Biol.* 2:2041-2053 (2004).
Rouskin, et al., "Genome-wide probing of RNA structure reveals active unfoldinng of mRNA strucutres in vivo", *Nature*, 505(7485):701-705 (2014).
Said, et al., "M1.3—a small scaffold for DNA origami", *Nanoscale*, 5(1):284-290 (2013).
Sanger, et al., "DNA sequencing with chain-terminating inhibitors", *Proc. Natl. Acad. Sci. U.S.A.*, 74(12):5463-5467(1977).
Santangelo, et al., "Nanostructred Probes for RNA Detection in Living Cells", *Annals of Biomedical Engineering*, 34(1):39-50 (2006).
Sattar, et al., "Ff-nano, short functionalized nanorods derived from Ff (f1, fd, or M13) filamentous bacteriophage", *Methods*, 6(316):1-13 (2015).
Seeman, et al., "Design of immobile nucleic acid junctions", *Biophys. J.*, 44(2):201-209 (1983).
Seeman, et al., "DNA nicks and nodes and nanotechnology", *Nano Lett.*, 1:22-26 (2001).
Seq Id: 1-139 Alignment (2020).
Shaik, et al., "CySpanningTree: Minimal Spanning Tree computation in Cytoscape [version 1; peer review: 1 approved, 1 approved with reservations]", *F1000 Research*, 4(476) 11 pages (2015).
Sharma, et al., "Control of self-assembly of DNA tubules through integration of gold nanoparticles", *Science*, 323(5910):112-6 (2009).
Shaw, et al., "Purification of functionalized DNA origami nanostructures", *ACS Nano*, 9(5):4968-4975 (2015).

(56) References Cited

OTHER PUBLICATIONS

Shih, et al., "A 1.7-kilobase single-stranded DNA that folds into a nanoscale octahedron", *Nature*, 427(6975):618-621 (2004).
Shilling, et al., "Structure and Function of Escherichia coli Type 1 Pili: New Insight into the Pathogenesis of Urinary Tract Infections", *The Journal of Infectious Diseases*, 183(Suppl.1): S36-S40 (2001).
Shepherd, et al., "Bioreproduction of pure, kilobase-scale single-stranded DNA", *Scientific Reports*, 9(6121):1-9 (2019).
Siegfried, et al.,"RNA motif discovery by SHAPE and mutational profiling (SHAPE-MaP)", *Nature Methods*, 11(9):959-965 (2014).
Sinclair, et al., "Generation of protein lattices by fusing proteins with matching rotational symmetry", *Nat. Nanotechnol.* 6(9):558-562 (2011).
Smola, et al., "Selective 2'-hydroxyl acylation analyzed by primer extension and mutational profiling (SHAPE-MaP) for direct, versatile and accurate RNA structure analysis", *Nat Protoc.*, 10(11):1643-1669 (2015).
Sobczak, et al., "Rapid folding of DNA into nanoscale shapes at constant temperature", *Science*, 338(6113):1458-1461 (2012).
Songsivilai, et al., "Bispecific antibody: a tool for diagnosis and treatment of disease", *Clin. Exp. Immunol.*, 79(3):15-321 (1990).
Specthrie, et al., "Construction of a microphage variant of filamentous bacteriophage", *Mol. Biol.*, 228(3):720-724 (1992).
Spink, et al., "Thermodynamics of forming a parallel DNA crossover", *Biophysical Journal*, 97(2):528-538 (2009).
Staple, et al., "Solution structure and thermodynamic investigation of the HIV-1 frameshift inducing element", *Journal of Molecular Biology*, 349(5):1011-1023 (2005).
Stephenson, et al., "Three-Dimensional RNA Structure of the major HIV-1 Packaging Signal Region", *Structure*, 21(6):951-962 (2013).
Sun, et al., "Casting inorganic structures with DNA molds", *Science*, 346(6210):1258361 (2014).
Tintore, et al., "DNA origami as a DNA repair nanosensor at the single-molecule level", *Angew Chem Int Ed Engl.*,52(30):7747-7750 (2013).
Tomley, et al., "M13 Phage Growth and Single-Stranded DNA Preparation", *Methods Mol. Biol.*, 58(43):359-362 (1996).
Torring, et al., "DNA origami: a quantum leap for self-assembly of complex structures", *Chem. Soc. Rev.*, 40(12):5636-46 (2011).
Tumpane, et al., "Triplex addressability as a Basis for Functional DNA Nanostructures", 7(12):3832-3839 (2007).
Ubaidurrahman, et al., "A Novel DNA Computing Based Encryption and Decryption Algorithm", *Procedia Comput Sci.*, 46:463-475 (2015).
Ui-Tei, et al., "Sensitive assay of RNA interference in *Drosophila* and Chinese hamster cultured cells using firefly luciferase gene as target", *FEBS Lett*, 479(3):79-82 (2000).
Untergasser, et al., "Primer3—new capabilities and interfaces", *Nucleic Acids Res.* 40(15):e115-e115 (2012).
Veneziano, et al., "Enzymatic Synthesis of gene-length single-stranded DNA", *bioRxiv* (2017).
Veneziano, et al., "Designer nanoscale DNA assemblies programmed from the top down", *Science*, 352(6293):1534 (2016).
Veneziano, et al., Supplementary Material for designer nanoscale DNA assemblies programmed from the top down, *Science*, (2016).
Vogel, et al., Hfq and its constellation of RNA, *Nature Reviews Microbiology*, 9(8):578-589 (2011).
Wahlestedt, et al., "Potent and nontoxic antisense oligonucleotides containing locked nucleic acids", *Proc. Natl Acad. Sci. USA*, 97(10):5633-5638 (2000).
Wang, "Double-stranded DNA homology produces a physical signature", *PNAS*, 107(28):12547-12552 (2010).
Wang, et al., "An atomic model of brome mosaic virus using direct electron detection and reasl-space optimization", *Nature Communications*, 5(4808) (2014).
Watts, et al., "Architecture and secondary structure of an entire HIV-1 RNA genome", *Nature*, 460(7256):711-716 (2009).
Wei, et al., "Complex shapes self-assembled from single-stranded DNA tiles", *Nature*, 485(7400):623-626 (2012).
Wilkinson, et al., "Selective 2'-hydroxyl acylation analyzed by primer extension (SHAPE): quantitative RNA structure analysis at single nucleotide resolution", *Nature Protocols*, 1(3)1610-1616 (2006).
Winfree, et al., "Design and self-assembly of two-dimensional DNA crystals", *Nature*, 394(6693):539-44 (1998).
Winter, et al., "Making antibodies by Phage Display Technology", *Annu Rev Immunol.*, 12:433-455 (1994).
Wong, et al., "Organic Data Memory Using the DNA Approach", *Communications of the ACM.*, 46:95-98 (2003).
Woo, et al., "Programmable molecular recognition based on the geometry of DNA nanostructures", *Nat. Chem.*, 3(8):620-7 (2011).
Wooddell, et al., "Use of asymmetric PCR to generate long primers and single-stranded DNA for incorporating cross-linking analogs into specific sites in a DNA probe", *Genome Res.* 6(9):886-892 (1996).
Wynn, et al., "HIV-1 drug discovery: targeting folded RNA structures with branched peptides", *Organic & Biomolecular Chemistry*, 13(21):5848-5858 (2015).
Xu, et al., "Design of 240,000 orthogonal 25mer DNA barcode probes", *PNAS*, 106(7):2289-2294 (2009).
Xuan, "Ultrasound-responsive block copolymer micelles based on a new amplification mechanism", *Langmuir*, 28(47):16463-16468 (2012).
Yan, et al., "DNA-templated self-assembly of protein arrays and highly conductive nanowires", *Science*, 301(5641):1882-1884 (2003).
Yang, et al., "Self-assembly of DNA rings from scaffold-free DNA tiles," *Nano Letters*, 13(4):1862-1866 (2013).
Yazdi, et al., "A Rewritable, Random-Access DNA-Based Storage System", *Scientific reports*, 5:14138 (2015).
Yim, et al., "The Essential Component in DNA-Based Information Storage System: Robust Error-Tolerating Module", *Frontiers in bioengineering and biotechnology*, 2:49 (2014).
Yuan, et al., "Solid-State Nanopore", *Nanoscale Res Lett.*, 13(1): 56 (2018).
Zhang, et al., "Complex wireframe DNA origami nanostructures with multi-arm junction vertices", *Nat. Nanotechnol.* 10(9):779-784 (2015).
Zhao, et al., Organizing DNA origami tiles into larger structures using preformed scaffold frames, *Nano Lett.*, 11(7):2997-3002 (2011).
Zhirnov, et al., "Nucleic acid memory", *Nat Mater.*, 15(4):366-70 (2016).
Zhou, et al. "A new biochromatography model based on DNA origami assembled PPARγ: construction and evaluation", *Anal. Bioanal. Chem.*, 409(12):3059-3065 (2017).
Zuckermann, et al., "Efficient method for the preparation of peptoids [oligo(N-substituted glycines)] by submonomer solid-phase synthesis", *J. Am. Chem. Soc.*, 114(26):10646-10647(1992).
Abramoff, et al., "Image processing with ImageJ", *Biophotonics Int.*, 11(2):36-42 (2004).
Ailenberg, et al., "An improved Huffman coding method for archiving text, images, and music characters in DNA", *BioTechniques.*, 47:747-754 (2009).
Angal, et al., "A single amino acid substitution abolishes the heterogeneity of chimeric mouse/human (lgG4) antibody", *Mol. Immunol.*, 30:105-08 (1993).
Benson, et al.,"DNA rendering of polyhedral meshes at the nanoscale", Nature, 523:441-444 (2015a).
Benson, et al., "Supplementary Information to DNA rendering of polyhedral meshes at the nanoscale", Nature, 523(7561):441-444 (2015b).
Brown, et al., "An easy-to-prepare mini-scaffold for DNA origami", *Nanoscale*, 7(4):16621-4 (2015).
Chandran, et al., "DNA origami: Folding DNA into Desired Shapes", 1-5, Fourth Warft Workshop on Brain Modeling and Supercomputing, (2009).
Chasteen, et al., "Eliminating helper phage from phage display", *Nucleic Acids Res.*, 34(21)e145: 1-11 (2006).
Cho, "An unnatural biopolymer", *Science*, 261(5126): 1303-1305 (1993).

(56) References Cited

OTHER PUBLICATIONS

Cui, et al., "An encryption scherne using DNA technology", 2008 Third International Conference on Bio-Inspired Computing: Theories and Applications., 37-41(2008).
Dotto, et al., "Initiation and termination of phage f1 plus-strand synthesis ", Proc. Natl. Acad. Sci. U.S.A., 79:7122-7126 (1982).
Douglas, et al., "Self-assembly of DNA into nanoscale three-dimensional shapes", Nature, 459(7425):414-418 (2009a).
Douglas, et al., "Rapid prototyping of 3D DNA-origami shapes with caDNAno", Nucleic Acids Res., 37:5001-5006 (2009B).
Elbashir, et al., "Duplexes of 21-nucleotide RNAs mediate RNA interference in cultured mammalian cells", Nature, 411:494-498 (2001).
Elbaz, et al., "Genetic encoding of DNA nanostructures and their self-assembly in living bacteria", Nat Commun, 7(11179 ):1-11 (2016).
Faber, et al., "Structural Rearrangements of HIV-1 Tat-responsive RNA upon Binding of Neomycin B*", The Journal of Biological Chemistry, 275:20660-20666 (2000).
Fan, et al., "Gating machinery of InsP3R channels revealed by electron cryomicroscopy", Nature, 527:336-341 (2015).
Fang, et al., "An unusual Topological Structure of the HIV-1 Rev Response Element" Cell, 155:594-605 (2013).
Geary, et al., "RNA nanostructures. A single-stranded architecture for cotranscriptional folding of RNA nanostructures", Science, 345:799-804 (2014).
Gradidsar, et al., "Design of a single-chain polypeptide tetrahedron assembled from coiled-coil segments", Nat. Chem. Biol., 9(6):362-366 (2013).
Grass, et al., "Robust chemical preservation of digital information on DNA in silica with error-correcting codes", Angew. Chern. Int. Ed., 54(8):2552-2555 (2015).
Gruber, et al., "Efficient tumor cell lysis mediated by a bispecific single chain antibody expressed in *Escherichia coli*.", J. Immunol., 152(11):5366 (1994).
Han, et al., "Single-stranded DNA and RNA origami", Science, 358(6369):1-25 (2017).
Howe, et al., "Seletive small-molecule inhibition of an RNA structural element", Nature, 526:672-677 (2015).
Iinuma et al., "Supplementary Material for Polyhedra self-assembled from tripods and Chracterized with 3D DNA-PAINT", Science, 344(6179):65-69 (2014).
Iinuma, et al., "Polyhedra Self-Assembled from DNA-PAINT", Science, 344(6179): 65-69 (2014b).
Irobalieva, et al., "Structural diversity of supercoiled DNA", Nat. Commun., 6(8440):1-10 (2015).
Jones, et al., "Nanomaterials. Programmable materials and the nature of the DNA bond", Science, 347(6224):840; 1260901-1-12060901-11 (2015).
Jones, et al., "Small-angle X-ray scattering-derived structure of the HIV-1 5' UTR reveals 3D tRNA mimicry", Proceedings of the National Academy of Sciences of the United States of America, 111:3395-3400 (2014).
Kazantsev, et al., "High-resolution structure of RNase P protein from Thermotoga maritima", Proceedings of the National Academy of Sciences of the United States of America. 100: 7497-7502 (2003).
Ke, et al., "Self-Assembled Water-Soluble Nucleic Acid Probe Tiles for Label-Free RNA Hybridization Assays", Science, 319(5860):180-183 (2008).
Ke, et al., "Three-dimensional structures self-assembled from DNA bricks", Science, 338(611):1177-1183 (2012).
Ke, et al., "Two design strategies for enhancement of multilayer-DNA-origarni folding: underwinding for specific intercalator rescue and staple-break positioning",Chem. Sci., 3(8):2587-2957 (2012B).
Kertesz, et al., "Genome-wide measurement of RNA secondary structure in yeast", Nature, 467:103-107 (2010).
Kim, et al. "Insertion and deletion mutants of FokI restriction endonuclease", J. Biol. Chem., 269:31978-31982 (1994B).
Kim, et al., "Chimeric restriction endonuclease", Proc. Natl. Acad. Sci. USA., 91:883-887 (1994A).
Li, et al., "Engineering nucleic acid structures for programmable molecular circuitry and intracellular biocomputation", Nature Chemistry, 9(11):1056-1067 (2017).
Li, et al., "Nucleic acid-based nanoengineering: novel structures for biomedical applications", Interface Focus, 1(5): 702-724 (2011).
Liedl, et al., "Self-assembly of 3D prestressed tensegrity structures from DNA", Nature Nanotechnology, 5:520-524 (2010).
Liu et al., "Crystalline two-dimensional DNA-origami arrays", Angew. Chem. Int. Ed. Engl., 50(1):264-267 (2011).
Liu, et al., "A DNA Nanostructure Platform for Directed Assembly of Synthetic Vaccines", Nano Letters, 12:4254-4259 (2012).
Liu, et al., "Diamond family of nanoparticle superlattices", Science, 351(6273):582-586 (2016b).
Lutz, et al., "Sequence-controlled Polymers", Science, 341(6146):628;1238149-1-1238149-8 (2013).
Martin, et al., "Magnesium-free self-assembly of multi-layer DNA objects", Nat. Commun., 3(1103):1-6 (2012).
Mercer, et al., "Structure and function of long noncoding RNAs in epigenetic regulation", Nature Structural & Molecular Biology. 20, 300-307 (2013).
Nafisi, et al., "Construction of a novel phagemid to produce custom DNA origami scaffolds", Synthetic Biology, 3(1), ysy015 (8 pages) (2018).
Nelson, "Droplet Actuation by Electrowetting-on-Dielectric (EWOD): A Review", Journal of Adhesion Science and Technology, 26:747-1771 (2012).
Nogales, et al., "Cryo-EM: A Uniquw Tool for the vizualization of Macromolecular Complexity", Molecular Cell, 58:677-689 (2015).
Olson, et al., "New Structue Sheds Light on Selective HIV-1 Genomic RNA Packaging", Viruses, 7:4826-4835 (2015).
Pan, et al., "Lattice-free prediction of three-dimensional structure of programmed DNA assemblies", Nature Communications., 5(5578): 1-7 (2014A).
Pasqualini, et al., "Organ targeting in vivo using phage dislay peptide libraries", Nature, 380:364-366 (1996).
Prim, "Shortest connection networls and some generalizations", Bell Syst. Tech. J., 36(6):1389-1401 (1957).
Rothemund, "Scaffolded DNA Origami: from Generalized Multicrossovers to Polygonal Networks", Nanotechnology: Science and Computation, 1-21 (2006b).
Rothemund, et al., "Folding DNA to create nanoscale shapes and patterns", Nature, 440(7082):297-302 (2006a).
Rouskin, et al., "Genome-wide probing of RNA structure reveals active unfoldinng of mRNA strucutres in vivo", Nature. 505:701-705 (2014).
Santangelo, et al., "Nanostructured Probes for RNA Detection in Living Cells", Annals of Biomedical Engineering, 34(1):39-50 (2006).
Sattar, et al. , "Ff-nano, short functionalized nanorods derived from Ff (f1, fd, or M13) filamentous bacteriophage", Front Microbiol., 6(316):1-13 (2015).
Seeman, et al., "DNA nicks and nodes and nanotechnology", Nano Lett., 1(1):22-26 (2001).
Seq Id No. 1-139 Alignment, 3 pages (Year: 2020).
Sun, et al., "Casting inorganic structures with DNA molds", Science, 346(6210):1-24 (2014).
Tomley, et al., "M13 Phage Growth and Single-Stranded DNA Preparation", Methods Mol. Biol., 58:359-362 (1996).
Torring, et al., "DNA origami: a quantum leap for self-assembly of complex structures", Chem. Soc. Rev., 40:5636-5646 (2011).
Tumpane, et al., "Triplex addressability as a Basis for Functional DNA Nanostructures", Nano Lett., 7(12):3832-3839 (2007).
Veneziano, "Supplementary Materials for designer nanoscale DNA assemblies programmed from the top down", Science, 352(6293):S1-S67 (2016).
Veneziano, et al., "Designer nanoscale DNA assemblies programmed from the top down", Science, 352(6293) 1534: 1-21 (2016).
Veneziano, et al., "Enzymatic Synthesis of gene-length single-stranded DNA", bioRxiv, 6 pages (2017).
Wang, et al., "An atomic model of brome mosaic virus using direct electron detection and real-space optimization", Nature Communications, 5(4808):1-12 (2014).

(56) References Cited

OTHER PUBLICATIONS

Watts, et al., "Architecture and secondary structure of an entire HIV-1 RNA genome", Nature, 460:711-716 (2009).
Winfree, et al., "Design and self-assembly of two-dimensional DNA crystals", Nature, 394(6693):539-544 (1998).
Woo, et al., "Programmable molecular recognition based on the geometry of DNA nanostructures", Nat. Chem., 3(8):620-627 (2011).
Yan, et al., "DNA-templated self-assembly of protein arrays and highly conductive nanowires", Science, 301:1882-1884 (2003).
Yazdi, et al., "A Rewritable, Random-Access DNA-Based Storage System", Scientific reports, 5(14138): 1-10 (2015).
Yim, et al., "The Essential Component in DNA-Based Information Storage System: Robust Error-Tolerating Module", Frontiers in bioengineering and biotechnology, 2(49):1-5 (2014).
Yuan, et al., "Solid-State Nanopore", Nanoscale Res Lett., 13: 56 (2018).
Zhang, et al., "Complex wirefram DNA origami nanostructure with multi-arm junction vertices", Nature Nanotechnology, 10: 779-785 (2015).

\* cited by examiner

COMPOSITIONS AND METHODS FOR MOLECULAR MEMORY STORAGE AND RETRIEVAL

CROSS REFERENCE TO RELATED APPLICATIONS

This application claims benefit of U.S. Provisional Application No. 62/866,571, filed Jun. 25, 2019, which is hereby incorporated herein by reference in its entirety.

STATEMENT REGARDING FEDERALLY SPONSORED RESEARCH

This invention was made with government support under Grant Nos. N00014-14-1-0609, N00014-16-1-2953, and N00014-17-1-2609 awarded by the Office of Naval Research, CMMI-1334109 awarded by the National Science Foundation, W911NF-18-1-0436 awarded by the Army Research Office, and R21-EB026008 awarded by the National Institutes of Health. The government has certain rights in the invention.

FIELD OF THE INVENTION

This invention is generally in the field of molecular memory retrieval and storage.

BACKGROUND OF THE INVENTION

Information and communication technologies generate vast amounts of data that will far eclipse today's data storage capacity. Information storage has gone through many stages of growth during the course of modern civilization. Libraries acting as repositories of information and using an indexed approach were categorized by various methods such as the Dewey Decimal System. Physical storage of digital information was initiated by programming to punch-card-based readers. The storage and growth of computers in modern society has led to digitization of information archives, and a rapid search of that data. However, this growth is outpacing the ability to store all of the information that needs to be inventoried. Memory materials must therefore be suitable for high-volume manufacturing. At the same time, they must have elevated information stability and limit the energy consumption and trailing environmental impacts that such storage will demand. Analysts estimate that global memory demand—at $3 \times 10^{24}$ bits—will exceed projected silicon supply in 2040 (Zhirnov V et al., Nat Mater. 23; 15(4):366-70 (2016)). To meet such requirements, flash-memory manufacturers would need ~$10^9$ kg of silicon wafers even though the total projected wafer supply is ~$10^7$-$10^8$ kg (Zhirnov V et al., Nat Mater. 23; 15(4):366-70 (2016)). Such forecasts motivate an exploration of unconventional materials with cost-competitive performance attributes.

DNA has previously been shown to be an outstanding material for use in archival or long-term information storage. The data storage density of DNA is massive, implemented up to 2.2 PB/gram of DNA (Goldman, N et al., Nature. 494, 77-80 (2013)), and the long-term fidelity of the information can last for thousands of years in its dry state with very little energy required for maintenance (Zhirnov, V et al., Nature materials. 15, 366-370 (2016)). Furthermore, the raw material is much more abundant than the ultra-pure wafer silicon required for the manufacture of the most prevalent current memory storage devices (Zhirnov, V et al., Nature materials. 15, 366-370 (2016)). This information storage density compares with archival tape-based storage that is currently the highest density storage medium by 8 orders of magnitude, with tape-based storage having a life-time rating of only 10-30 years (Bornholt, J et al., 21th ACM International Conference on Architectural Support for Programming Languages and Operating Systems. (2016)).

Previous applications using DNA to store information have been implemented as the storage of books, sonnets, sound clips, images, and online webpages (Goldman, N et al., Nature. 494, 77-80 (2013); Church, G M et al., Science. 337, 1628 (2012); Yazdi, S M et al., Scientific reports. 5, 14138 (2015); Yim, A K et al., Frontiers in bioengineering and biotechnology. 2, 49 (2014)). In each case, DNA memory has been stored in either linear double-stranded (~700-1,000 nucleotides) or short single-stranded (~125 nucleotide) oligonucleotide sequences using a variety of encoding strategies. These coding strategies have been simple direct to base (Church, G M et al., Science. 337, 1628 (2012); Clelland, C T et al., Nature. 399, 533-534 (1999); Wong, P C et al., Communications of the ACM. 46, 95-98 (2003)), Huffman code (Goldman, N et al., Nature. 494, 77-80 (2013); Bornholt, J et al., 21th ACM International Conference on Architectural Support for Programming Languages and Operating Systems. (2016); Ailenberg, M et al., BioTechniques. 47, 747-754 (2009)), compressed (Yim, A K et al., Frontiers in bioengineering and biotechnology. 2, 49 (2014)), and encrypted (Babaei, M., Nat Comput. 12, 101-107 (2013); Cui, G Z et al., 2008 Third International Conference on Bio-Inspired Computing: Theories and Applications. 37-41(2008); Gehani, A et al., Lect Notes Comput Sc. 2950, 167-188 (2004); Leier, A et al., Biosystems. 57, 13-22 (2000); UbaidurRahman, N H et al., Procedia Comput Sci. 46, 463-475 (2015)). Random access of direct encoded memory have been demonstrated by PCR methods using barcoding strategies and spatial segregation of information pools into distinct wells (Bornholt, J et al., 21th ACM International Conference on Architectural Support for Programming Languages and Operating Systems. (2016); Yazdi, S M et al., Scientific reports. 5, 14138 (2015)), as well as hybridization (Banal, et al., bioRxiv 2020.02.05.936369, doi:10.1101/2020.02.05.936369, Lin, et al., Nature Communications, volume 11, Article number: 2981 (2020)), and content-based image similarity search (Bee, et al., bioRxiv 2020.05.25.115477; doi:10.1101/2020.05.25.115477), which may include pull down by beads, isothermal amplification by transcription, or FACS-based sorting.

These approaches have implementation limitations in sorting and retrieval of chunks of specific DNA to group into a block, or chunk, or page of information. The approaches rely on a capability to have an intermediate separation and storage unit distinct from the synthesis and distinct from the sequencing device. They typically rely on (1) synthesis of a set of information or DNA in a pool encoding a group of data that should be stored together such as a file or a block of memory (2) capture of the DNA into a droplet or on a surface, or on a bead, or within a bead or on a column support or otherwise separated into distinct groups (3) accessed from the structured location by displacement, electrostatic release, transcription, replication (e.g. biological or PCR or isothermal amplification such as with phi29 polymerase) or by sorting by FACS or magnetic bead or other methods known in the art and (4) sequencing the accessed material by nanopore, methods of sequencing by synthesis used in Illumina, PacBio (with phi29 polymerase variants), or 454 sequencing. To obtain the sequenced material, the retrieved information or DNA fragments must be deprotected and amplified, or transcribed and reverse-transcribed, and amplified, and barcoded to allow for subsequent sequencing. Thus the 4 global steps here are laborious and prone to failure without significant automation and methods of automatic sorting and retrieval and storage.

The interface between DNA, biology, and silicon computing has only just begun to be explored. The semiconductor industry is in need of alternative information storage capabilities because of the increase in the data being stored across the world.

Thus, it is also an objective of the invention to provide improved compositions and methods for storage and retrieval of molecular data.

SUMMARY OF THE INVENTION

Compositions and methods for the storage, organization, access, and retrieval of information encoded by sequence controlled polymers such as data storage nucleic acids are provided.

For example, surfaces and objects including sequence-controlled polymers hybridized or otherwise linked thereto are provided. Typically, the surface or object includes at least one, preferably a plurality of oligonucleotides of between, for example, about 20 and 100 nucleotides in length linked thereto. Each oligonucleotide can be hybridized by complementary base pairing to a sequence controlled polymer such as a data storage nucleic acid including a nucleic acid sequence of, for example, between about 50 and 50,000 nucleotides encoding data. Surfaces and objects include, but are not limited to, beads, chips, DNA structures including DNA nanostructures (e.g., DNA origami), hydrogels, glass slides, mineral surfaces, and plates and wells, including, for example, microtiter plates or other multiwell dishes. The surface may be a single micron-scale well or a plurality of wells on a chip, so while an individual well may contain a limited number (e.g., from 1-10, inclusive) of oligonucleotides, the chip is scalable, and may contain tens, hundreds, or thousands of oligonucleotides.

In some embodiments, the surface or object is a chip further including a nanopore adjacent to each oligonucleotide, or a multiwell plate, each well including a different oligonucleotide and reagents suitable for sequencing the data storage nucleic acid. Such surfaces and objects can be used to store the sequence controlled polymers at specific locations or wells based on hybridization of the sequence controlled polymer to the oligonucleotide. As such, the oligonucleotide can serve as an "address" which can be activated for on demand sequencing of the resident sequence controlled polymer when retrieval of the data encoded therein is desired.

Thus, systems including the surfaces and objects are also provided. The systems typically integrate a nucleic acid sequencing platform with a surface or object such that the sequence controlled polymer, e.g., a data storage nucleic acid, can be selectively sequenced by providing suitable stimulus, for example an electrical stimulation, that activates sequencing at the location of the data storage nucleic acid. Sequencing platforms include, but are not limited to, nanopore, Sanger, Single Molecule, Real-time Sequencing (SMRS), and sequencing by synthesis. The electrical signal can be controlled by and/or delivered by a computer interface.

Methods for address printing (e.g., placing oligonucleotides on a surface or object) are also provided. The methods can, for example, utilize electrowetting to drive a droplet including a plurality of sequence controlled polymers, e.g., data storage nucleic acids, over an array of address oligonucleotides under conditions suitable for a data storage nucleic acid to hybridize by complementary base pairing to a corresponding address oligonucleotide, optionally followed by washing off unbound data storage nucleic acids. In some embodiments, the oligonucleotides are arrayed on a surface or object including or composed of a dielectric material, optionally wherein the dielectric material includes silica.

Compositions and methods of utilizing recombinant bacteriophage (also referred to herein as phage) for data storage and retrieval of sequence controlled polymers such as data storage nucleic acids, as well as in display and screening of other inserts such as expression constructs encoding genes or other open reading frames, are also provided. For example, a phagemid can include a nucleic acid including nucleic acid sequences encoding data or an expression construct, two barcodes, a bacteriophage origin of replication, and a bacteriophage packaging signal. In some embodiments, the phagemid is circular and optionally, but preferably single stranded. Typically, the sequence encoding insert is separated from the sequences encoding the bacteriophage origin of replication, bacteriophage packaging signal, selectable marker, or a combination thereof by the barcodes, which can be the same or different sequences. The nucleic acid optionally, but preferably, encodes a selectable marker, and optionally, but preferably does not encode a bacterial origin of replication. In some embodiments, the nucleic acid further includes a nucleic acid sequence encoding between about 1, 2, 3, 4, 5, 6, 7, 8, or more, but preferably not all, bacteriophage (e.g., M13) capsid proteins, or fusions proteins thereof. In particular embodiments, the bacteriophage origin of replication is f1, the selectable marker is an antibiotic resistant gene, the nucleic acid sequence encoding the insert is between about 50 and 50,000 nucleotides in length, the bacteriophage capsid protein(s) are M13 capsid protein(s) or fusion protein(s) thereof, or a combination thereof. When the insert encodes data, the nucleic acid can be referred to as a data storage nucleic acid, and can be used to store data. An exemplary expression construct encodes a target polypeptide for display (e.g., an antigen binding protein) fused to a capsid protein (e.g., g3 and/or g8 from M13). Such phage can be used for phage display and selection.

Methods of making the phage-based nucleic acid are also provided. In some embodiments, the methods include incubating a single stranded vector template including the reverse complementary sequence to the two barcodes, the bacteriophage origin of replication, and the bacteriophage packaging signal with a single stranded precursor nucleic acid including the nucleic acid sequences encoding the insert and the two barcodes under conditions that allow the vector template and single stranded precursor nucleic acid to hybridize at the barcodes sequences, and polymerase to extend the single stranded precursor nucleic acid over the vector template to form a phagemid including nucleic acid sequences encoding the insert, two barcodes, a bacteriophage origin of replication, and a bacteriophage packaging signal. Such condition may include, for example, annealing of the barcodes in the presence of a specific buffer containing salts and/or mild detergents. In some embodiments, the 3' end of the vector template is blocked to prevent extension of the vector template by the polymerase and leading to a single stranded nucleic acid phagemid. The 5' end of the precursor nucleic acid may be phosphorylated. The methods can further include ligating the extended precursor nucleic acid to form a circular nucleic acid. In some embodiments, the vector template is linked to a surface.

Protein-nucleic acid complexes including phagemid and capsid proteins are also provided. In exemplary embodiments, the bacteriophage capsid proteins are g7 and g9 from M13.

Methods of introducing phage-based nucleic acids into cells are also provided. The methods can include transforming or transfecting bacterial cells with phagemid optionally, but preferably, wherein the bacteria encodes helper plasmids that allow phagemid replication and assembly into a bacteriophage, or secretion of the phagemid into the media.

In some embodiments, protein-nucleic acid complexes including phagemid and capsid proteins are formed in vitro and used to infect bacteria directly, optionally, but preferably, wherein the bacteria encodes helper plasmids that allow phagemid replication and assembly into a bacteriophage, or secretion of the phagemid into the media. In exemplary embodiments, the bacteriophage capsid proteins are g7 and g9 from M13, the bacteria F-pili E. coli, or a combination thereof.

Additional methods of data storage and retrieval are also provided, and may include selectively linking a bacteriophage to a desired physical location on a surface. Typically, the bacteriophage includes a genome including a nucleic acid encoding data and capsid protein linked to a barcode sequence, wherein the surface includes the reverse complement of the barcode at the physical location, and the bacteriophage and the surface are brought into contact under conditions that the allow the phage's barcode to hybridize to the reverse complement on the surface. Surfaces include, but are not limited to, a bead, a chip, a well, a glass slide, a mineral surface, or a plate.

Additional methods of retrieving data from, for example, a library of different bacteriophage are also provided. The methods typically include contacting the library with E. coli, wherein the E. coli expresses a receptor that can bind to a ligand linked to a bacteriophage. The library typically includes bacteriophage having different ligands linked thereto, and amplification of the E. coli leads to selective amplification of the bacteriophage linked to the ligand that can bind thereto. In some embodiments, the ligand is an antigen binding protein, and the receptor is the antigen that binds thereto, or the receptor is an antigen binding protein and the ligand is the antigen that binds thereto.

Similarly, methods of panning a library of different bacteriophage for a target bacteriophage are also provided. Typically, different bacteriophage in the library have different genomes encoding different ligands fused to a bacteriophage capsid protein, and displays the ligand as part of its capsid head. E. coli expressing a receptor that can bind to a ligand encoded by at least one target bacteriophage genome in the library are contacted with the library, and amplification of the E. coli leads to selective amplification of the bacteriophage linked to the ligand that can bind thereto.

Any of the disclosed methods can further include isolating and/or sequencing a sequence controlled polymer or other nucleic acid. Thus, in some embodiments, the genome of a data storage phagemid or other phage genome, optionally selectively amplified, is isolated and/or sequenced.

BRIEF DESCRIPTION OF THE DRAWINGS

FIGS. 3A and 3B are maps of exemplary vector templates. FIG. 3C is a map of an exemplary digital information/variable DNA insert. FIG. 3D is an exemplary workflow which includes cloning the single strand phage genome, as well as optional in vitro phage infection head protein assembly for rapid infection of cloned DNA. In the schematic the in vitro assembly of the head proteins and infection is illustrated with M13 phage and transformation of E. coli.

FIG. 4A is a map of an exemplary vector template. FIG. 4B is a map of an exemplary variable DNA insert for protein expression. FIG. 4C is an exemplary workflow which includes cloning the single strand phage genome, as well as optional in vitro phage infection head protein assembly for rapid infection of cloned DNA. In the schematic the in vitro assembly of the head proteins and infection is illustrated with M13 phage and transformation of E. coli.

DETAILED DESCRIPTION OF THE INVENTION

I. Definitions

Figure 1:
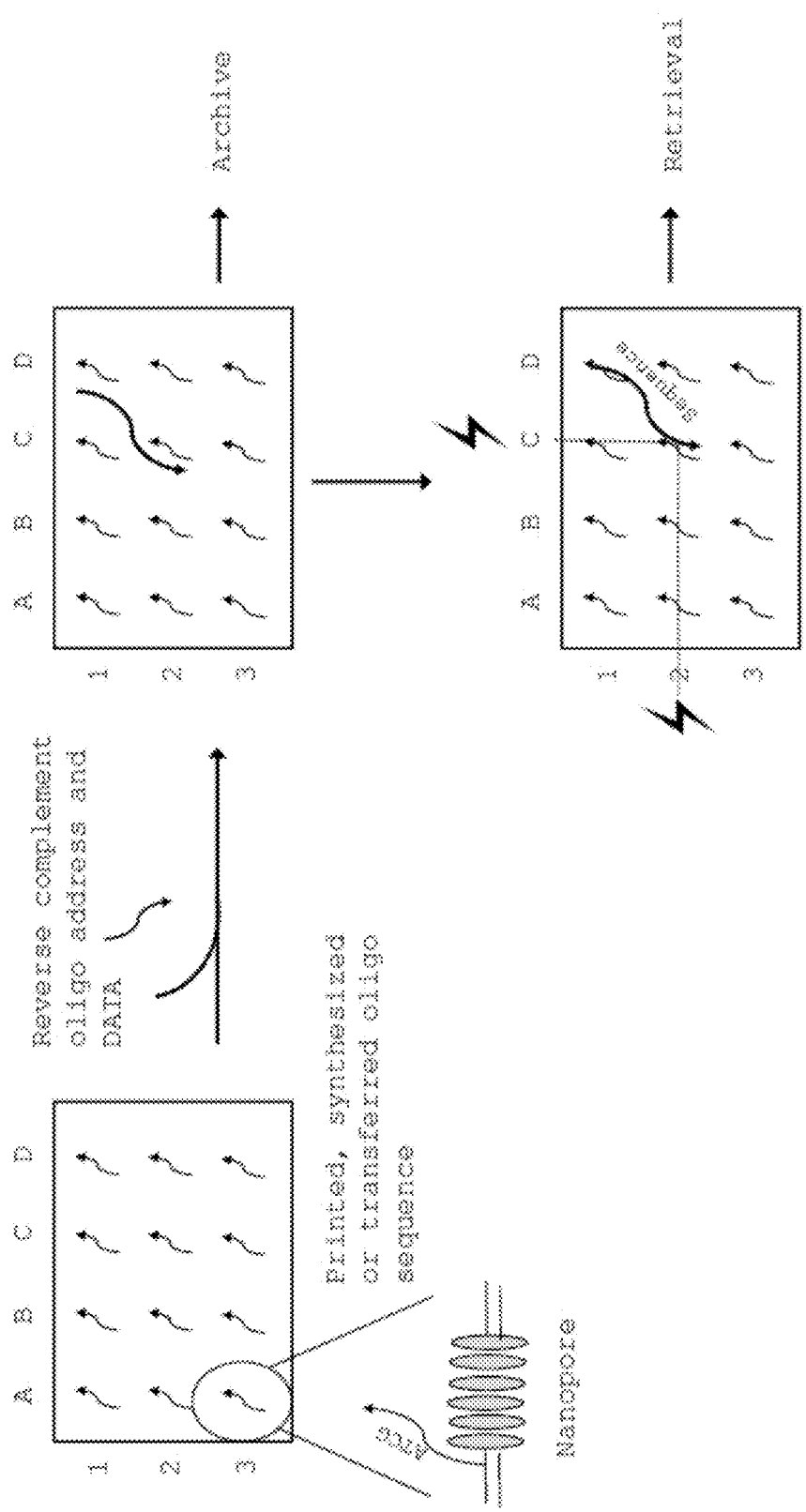
FIG. 1 is a flow diagram illustrating use of spatial addressing for nanopore sequencing. A schematic is shown representing a sequencing chip that can be triggered at a certain location with a known sequence being deposited in that location by hybridization to an address sequence. Sequencing in that location and translation to the original digital information will allow on-demand retrieval of the information.

The term "payload" refers to the actual body of data for transmission or for storage or computation. For example, in nucleic acid memory storage, the payload is encoded in the specified nucleotide sequence. The terms "desired data", "desired information" or "desired media" are used interchangeably to specify the payload information that is contained in the bit stream encoded sequence.

The term "bit stream encoded sequence" is any natural or synthetic sequence-controlled polymer sequence that encodes for data to be stored. For example, when nucleic acid is used to store data, the "bit stream encoded sequence" is the nucleic acid sequence that corresponds to the data that is encoded. Bit stream-encoded nucleic acid can be in the form of a linear nucleic acid sequence, a two-dimensional nucleic acid object or a three-dimensional nucleic acid object. Bit stream-encoded nucleic acid can include a sequence that is synthesized, or naturally occurring.

The term "bit" is a contraction of "binary digit". Commonly "bit" refers to a basic capacity of information in computing and telecommunications. A "bit" conventionally represents either 1 or 0 (one or zero) only, though other codes can be used with nucleic acids that contain 4 nucleotide possibilities (ATGC) at every position, and higher-order codecs including sequential 2-, 3-, 4-, etc. nucleotides can alternatively be employed to represent bits, letters, or words.

The terms "nucleic acid molecule," "nucleic acid sequence," "nucleic acid fragment," "oligonucleotide" and "polynucleotide" are used interchangeably and are intended to include, but not limited to, a polymeric form of nucleotides that may have various lengths, either deoxyribonucleotides (DNA) or ribonucleotides (RNA), or analogs or modified nucleotides thereof, including, but not limited to locked nucleic acids (LNA) and peptide nucleic acids (PNA). An oligonucleotide is typically composed of a specific sequence of four nucleotide bases: adenine (A); cytosine (C); guanine (G); and thymine (T) (uracil (U) for thymine (T) when the polynucleotide is RNA). Thus, the term "oligonucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Oligonucleotides may optionally include one or more non-standard nucleotide(s), nucleotide analog(s) and/or modified nucleotides.

The terms "sequence controlled polymer", "sequence controlled macromolecule" and "memory polymer" refer to a macro-molecule that is composed of two or more distinct monomer units sequentially arranged in a specific, non-random manner, as a polymer "chain". The arrangement of the two or more distinct monomer units constitutes a precise molecular "signature", or "code" within the polymer chain. Sequence controlled polymers can be biological polymers (i.e., biopolymers), or synthetic polymers. Exemplary sequence-controlled biopolymers include nucleic acids, polypeptides or proteins, linear or branched carbohydrate chains, or other sequence controlled polymers that encode a format of information. Exemplary sequence controlled polymers are described in Lutz, et al., Science, 341, 1238149 (2013).

The term "antibody" is used in the broadest sense unless clearly indicated otherwise. Therefore, an "antibody" can be naturally occurring or man-made such as monoclonal antibodies produced by conventional hybridoma technology. Antibodies include monoclonal and polyclonal antibodies as well as fragments containing the antigen-binding domain and/or one or more complementarity determining regions of these antibodies. As used herein, the term "antibody" refers to any form of antibody or antigen binding fragment thereof that specifically binds its antigen, or fragments or fusions thereof and/or exhibits the desired biological activity and specifically covers monoclonal antibodies (including full length monoclonal antibodies), polyclonal antibodies, multispecific antibodies (e.g., bispecific antibodies), and antibody fragments. Any specific antibody can be used in the methods and compositions provided herein. Thus, in one embodiment the term "antibody" encompasses a molecule comprising at least one variable region from a light chain immunoglobulin molecule and at least one variable region from a heavy chain molecule that in combination form a specific binding site for the target antigen. In one embodiment, the antibody is an IgG antibody. For example, the antibody is a IgG1, IgG2, IgG3, or IgG4 antibody. An "antibody fragment" or "antigen binding fragment" of an antibody is defined as at least a portion of the variable region of the immunoglobulin molecule that binds to its target, i.e., the antigen-binding region. The antibody of the present methods and compositions can be monoclonal or polyclonal. An antibody can be in the form of an antigen binding antibody fragment including a Fab fragment, $F(ab')_2$ fragment, a single chain variable region, and the like. Fragments of intact molecules can be generated using methods well known in the art and include enzymatic digestion and recombinant means.

As used herein, any form of the "antigen" can be used to generate an antigen-specific antibody. The antigen may contain a single epitope, multiple epitopes, or can be the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell.

As used herein, the term "construct" and "cassette" refer to a recombinant genetic molecule having one or more isolated polynucleotide sequences. Genetic constructs used for transgene expression in a host organism typically include in the 5'-3' direction, a promoter sequence; a sequence encoding a gene of interest; and a termination sequence. The construct may also include selectable marker gene(s) and other regulatory elements for expression.

As used herein, the term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other forms the values may range in value either above or below the stated value in a range of approx. +/−5%; in other forms the values may range in value either above or below the stated value in a range of approx. +/−2%; in other forms the values may range in value either above or below the stated value in a range of approx. +/−1%. The preceding ranges are intended to be made clear by context, and no further limitation is implied.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a ligand is disclosed and discussed and a number of modifications that can be made to a number of molecules including the ligand are discussed, each and every combination and permutation of ligand and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials.

These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

II. Sequence Controlled Polymers for Data Storage

Compositions and methods for the storage, organization, access, and retrieval of information of sequence controlled polymers, such as nucleic acid sequences, have been developed. For example, information can be provided in the form of a data storage nucleic acid, for example a single-stranded nucleic acid such as DNA. In some embodiments, the methods include location-based addressing of nucleic acid memory, where nucleic acids are used to encode digital information within the sequence of the nucleic acid polymer (e.g., deoxyribonucleic acids, ribonucleic acids, or xenonucleic acid), that can be addressed (e.g., on either the 5' and/or 3' end of the polymer) to direct the nucleic acid to a certain specific (e.g., geometric) location on, for example, an etched silica wafer, glass surface, or well for purposes of organization and sequencing.

A. Information to be Stored

Compositions and methods of storing, organizing, manipulating and accessing information as physical memory are provided, and can be used to store, access or record information encoded as sequence controlled polymers, such as nucleic acid sequences, or polypeptide or carbohydrate or other biopolymer sequences.

The information can include any desired media in any format. In some embodiments, a desired media includes any kind of media useful to communicate information. The information or media can be obtained from any source known in the art, including exemplary print media, such as books, magazines, newspapers, etc.), televisual media, including movies, video games, televised news, cartoons, images, etc.), audible media, such as music, or radio broadcasts, cellular phone data, various kinds of software, and media available on the Internet, such as media in an html format, databases, government or private records documents, financial data or ledgers, or any other digital format, or databases of cDNA or natural DNA sequences. Internet data or other information storage data including data with properties that need to be classified automatically through machine learning or other classification strategies may also benefit from the proposed molecular memory approach. Monitoring or profiling data from flights, transportation, military, or other sources may also be of use, together with financial data, banking data, health records, patient data, and personnel-related data, and autonomous vehicle data. For example, in some embodiments, the desired media is the text of a book, or the text of one or more chapters of a book, or the text of one line of one page of a book.

B. Sequence Controlled Polymers

Sequence controlled polymers such as those encoding bitstream data can be biopolymers, such as DNA or polypeptides, or synthetic biopolymers, such as peptidomimetics. A non-limiting list of sequence-controlled polymers includes naturally occurring nucleic acids, non-naturally occurring nucleic acids, naturally occurring amino acids, non-naturally occurring amino acids, peptidomimetics, such as polypeptides formed from alpha peptides, beta peptides, delta peptides, gamma peptides and combinations, carbohydrates, block co-polymers, and combinations thereof. Sequence-defined unnatural polymers closely resemble biopolymers, such as polymers incorporating non-canonical amino acids. e.g., peptidomimetics, such as β-peptides (Gellman, S H. *Acc. Chem. Res.*, 31, 173-180 (1998)), peptide nucleic acids (PNA), peptoids or poly-N-substituted glycines (Zuckermann, et al., *J. Am. Chem. Soc.*, 1 14, 10646-10647(1992)), Oligocarbamates (Cho, C Y et al., *Science*, 261, 1303-1305(1993), glycomacromolecules, Nylon-type polyamides, and vinyl copolymers.

A suitable sequence controlled polymer is one that is also compatible with the selected form of storage and/or retrieval disclosed herein. A preferred sequence-controlled polymer is a nucleic acid, such as single or double-stranded DNA, or RNA, most preferably single stranded DNA. Nucleic acid-based sequence controlled polymers are also referred to herein as data storage nucleic acids.

Digital information can be encoded in sequence controlled polymers such as DNA sequences by a number of methods including by solid state synthesis as known in the art, or by enzymatic de novo synthesis using, for example terminal deoxytransferase (tdt), with 5' and 3' complementary primers to the cloning plasmid. The stable maintenance of the polymer (e.g., DNA) is the only limiting factor for the cloning and archival of the polymer.

Enzymatic and non-enzymatic synthesis of sequence-defined non-natural polymers can be achieved through templated polymerization (reviewed in Brudno Y et al., *Chem Biol.*; 16(3): 265-276 (2009)). Deoxyribonucleic acid polymers (DNA) and similar polymers contain defined bases or side chains that can be used to encode digital information in the sequence of these chemical adducts. Canonical sequences of DNA, for example, include adenine (A), thymidine (T), cytosine (C), and guanosine (G). Many other possible modified or non-canonical bases exist, as well as sugar and phosphate backbone modifications, but the technology for digital information storage on the polymer sequence remains the same. In some embodiments, higher densities of information can be achieved by increasing the chemical diversity of oligonucleotides by incorporating chemical functionalities that are not present in natural RNA and DNA into nucleotide triphosphates. In this manner, more than 100 functionalized nucleotides have been incorporated into DNA and RNA, including those containing nucleophilic groups such as amines and thiols, electrophilic groups such as acrylates and aldehydes, proton donors and acceptors such as imidazole, pyridine, and guanidinium groups, and reactive groups such as cyanoborohydride. A further exemplary polymer modification involves replacing or modifying the phosphate-ribose nucleic acid backbone. For example, modification of the 2'-hydroxyl group of RNA increases the stability of RNA and confers nuclease resistance. A number of different 2' groups have been successfully incorporated in a sequence-specific manner using polymerase enzymes including fluoro-, amino-, methoxy-, and amido-ribonucleotides. Modifications at the 4' position including azide, alkyne, and acyl moieties. The polymerase-mediated incorporation of backbones that do not contain a ribose group can also be used. In some embodiments, enzymatic polymerization of locked nucleic acid (LNA) triphosphates on DNA and RNA templates is also used. In addition to substituting the sugar group of the backbone, the phosphate group can also be modified to generate sequence-defined nonnatural polymers using polymerase enzymes. Phosphate-backbone substitutions, in which one of the non-bridging oxygen atoms is replaced, can confer greater nuclease resistance, lipophilicity, and polarizability. In a similar manner, an oxygen atom in the phosphate group can also be replaced with selenium to form phosphoroselenoate oligonucleotides.

C. Conversion of Data into Polymer Sequences

The digital information can be encoded with several strategies including standard binary to base conversion, binary to trit, binary to quartinary code, encrypted, compressed, or generated by any known mechanism with any known standard encoding. The scheme used is agnostic to the approaches described herein. Preferably, the approach used should allow for having the memory blocks kept in fragments of 50 nt, 51 nt, 52 nt, or greater than 52 nt, up to 10,000 nt, 10,001 nt, or greater than 10,001 nt up to 50,000 nt.

In some embodiments, a portion or portions of a digital format of information, such as an html format of information or any other digital format such as a book with text and/or images, audio, or movie data, is converted to bits, i.e. zeros and ones. In some embodiments, the information can be otherwise converted from one format (e.g., text) to other formats such as through compression by Lempel-Ziz-Markov chain algorithm (LZMA) or other methods of compression, or through encryption such as by Advanced Encryption Standard (AES) or other methods of encryption. Other formats of information that can be converted to bits are known to those of skill in the art.

Therefore, in some embodiments, the methods include converting a format of information into one or more bit sequences of a bit stream. One or more bit sequences can be converted into one or more corresponding polymer subunits. In some embodiments, bit sequences are converted to nucleic acid sequences. Therefore, when the desired information exists in one or more bit sequences, the methods can include converting the one or more bit sequences into one or more corresponding nucleic acid sequences.

In exemplary embodiments, a digital file, encoded on a computer as a bit stream of 0's and 1's, is reversibly converted to a nucleic acid sequence using any of the methods known in the art. In some embodiments, an oligonucleotide or DNA using a 1 bit per base encoding (A or C=0; T or G=1) to form a corresponding encoded oligonucleotide sequence, i.e. the oligonucleotide sequence corresponds to or encodes for the bit sequence. In some embodiments the choice of digital format, for example the encryption salt, and the choice of bitstream to equivalent nucleic acid sequence, for example choice of A rather than C, is optimized such that the sequence repetition and sequence self-complementarity are avoided, identified by methods known to the art.

The nucleic acid sequence generated from the bit stream data of a desired media is termed the "bit stream encoded sequence". The bit stream data encoded within the long scaffold sequence is typically "broken-up" into fragments. For example, data can be fragmented into any size range from about 100 to about 1,000,000 nucleotides, such as from about 375 to about 51,000 bases, inclusive, per object, for example, 500 bp up to 50,000 bp. In the digital storage field this is conceptually synonymous with "page" or "block". The bit stream-encoded nucleic acid sequence is synthesized by any known strategy, and is amplified or purified using a variety of known techniques (i.e., asymmetric PCR, bead-based purification and separation, cloning and purification). In some embodiments, the memory page will have identifying information as part of each sequence, including a file format signature, a sequence encoding an encryption salt, a unique identifying page number, a memory block length, and a sequence for DNA amplification.

In an exemplary embodiment, a digital file is compressed, for example, using the LZMA method, or the file is encrypted, for example, using AES128 encryption using a supplied password and salt. The compressed or encrypted bitstream of 0s and 1s is converted to a nucleic acid sequence that is chosen such that there are a minimum number of repeating or complementary sequences greater than 7 nucleotides. If such sequences exist, alternative sequences with equivalent bitstream data are chosen. The sequence can then be prepended as a sequence encoding one or more of a forward primer for PCR, an identifier primer, a file-type indicating sequence, a length of the memory block stored, the size of the stored memory block, and an identifying sequence of which page of the total memory the sequence is storing. To the 3' end of the bitstream sequence, a message end signature sequence can be appended. In some embodiments, the 3' end sequence also encodes slack or nonsense sequences, which are added to fill up the total needed length for the chosen geometry. The 3'end can also include a reverse identifier primer, and a reverse primer for PCR. This sequence is then synthesized.

Methods to synthesize nucleic acids are known in the art. For example, in some embodiments, nucleic acids are synthesized using a GBlock from Integrated DNA Technologies, Inc., or using template-free synthesis by Molecular Assemblies, Inc., or by chip-based solid-state synthesis by Agilent, Inc., or Twist Bioscience, Inc. In some embodiments, Asymmetric polymerase chain reaction (aPCR) is used to generate the single stranded nucleic acid sequence that contains the sequence converted from the bitstream (i.e., the bit stream encoded sequence), or it may directly be encoded in and produced by living bacteria or phage.

In some embodiments, only one of the strands will be used.

In some embodiments, the methods include providing a nucleic acid sequence from a pool containing a multiplicity of similar or different sequences is provided. In some embodiments, the pool is a database of known sequences. For example, in certain embodiments a discrete "block" of information is contained within a pool of nucleic acid sequences ranging from about 100-1,000,000 bases in size, though this upper limit is theoretically unlimited.

In some embodiments, the nucleic acid sequences within a pool of multiple nucleic acid sequences share one or more common sequences. When nucleic acids that are provided are selected from a pool of sequences, the selection process can be carried out manually, for example, by selection based on user-preference, or automatically. Methods of storage and retrieval are discussed in more detail below.

In some embodiments, the bit stream encoded nucleic acid sequence is not the same sequence as chromosomal DNA, or mRNA, or prokaryotic DNA. For example, in some embodiments, the entire bit stream encoded sequence has less than 20% sequence identity to a naturally-occurring nucleic acid sequence, for example, less than 10% identity, or less than 5% identity, or less than 1% identity, up to 0.001% identity. Therefore, in some embodiments, bit stream encoded sequence of the desired media is not the nucleic acid sequence of an entire gene. For example, in some embodiments the bit stream encoded sequence of the desired media is not the same sequence as the open-reading frame (ORF) of a gene. In some embodiments, bit stream encoded sequence of the desired media is not the same nucleic acid sequence as a plasmid, such as a cloning vector. Therefore, in some embodiments, bit stream encoded sequence of the desired media does not include one or more sequence motifs associated with the start of transcription of a gene, such as a promoter sequence, an operator sequence, a response element, an activator, etc. In some embodiments, bit stream encoded sequence of the desired media is not a nucleic acid sequence of a viral genome, such as a single-stranded RNA or single-stranded DNA virus.

In other embodiments, the bitstream sequences are composed of the sequences of cDNAs, genes, protein sequences, protein coding open reading frames, or biological sequences that together in a pool form a database of biological sequences.

In some embodiments, the sequence controlled polymer is a user-defined single stranded nucleic acid that includes one or more pieces of digital bitstream data encoded by its sequence. Arbitrary sequence can be used to encode digital files, packaged into phage that can be desiccated, siliconized, and can display molecular identifiers as discussed in more detail below. Strategies for data storage using nucleic acid scaffold sequences are described in more detail in WO 2017/189914, which is specifically incorporated by reference herein in its entirety, and can be used to design target nucleic acid sequences utilized in the disclosed storage and retrieval compositions and methods.

D. Molecular Identifiers

Many of the applications and methods described herein include organizing, storing, and/or retrieving information based on use of a molecular identifiers. As used herein "identifier," "barcode," "address," and "universal adaptor" are used to describe a molecular means that can be used to identify a sequence controlled polymer. For example, nucleic acid molecules from different samples can be pooled together and subjected to massively parallel sequencing in order to efficiently determine sequence information from numerous different samples. Prior to sequencing, identifiers can be added to the nucleic acid molecules, and this facilitates grouping, analysis, and interpretation of information. As another example, molecular barcodes can be added to target nucleic acid molecules prior to amplification, so that the replicates of the initial target molecule can subsequently be identified and grouped together. See, e.g., U.S. Published Application 2020/0181602.

Thus, the sequence controlled polymers, in additional to encoding data, may also include one or more identifier sequences. The inserts and vector templates described herein may also include one or more identifier sequences. For example, in some embodiments, the identifier can be a barcode including 6 or more nucleotides. In some embodiments, the barcode sequence is between 6 and 100 nucleotides, inclusive, or any subrange or individual integer number of nucleotides there between.

The sequence of the identifier can be a known, degenerate, and/or random sequence. The sequence can be arbitrary.

The identifier can be at the 5' end, 3' end, or in the interior of the sequence controlled polymer.

The identifier can be part of the data storage sequence, or can be distinct therefrom. Thus, in some embodiments, the barcode(s) or addresses are separate from the data storage sequence and provide localization and hybridization information without encoding the data for which storage is desired.

In addition of identification, grouping, and/or analysis, some of the compositions and methods disclosed herein may also utilize the identifier to facilitate physical sorting, organization, storage, and/or retrieval, including selective retrieval, of the sets, subsets, or individual sequence controlled polymers. For example, hybridization of a single stranded identifier of the sequence controlled polymer to a single strand oligonucleotide having the reverse complementary sequence thereof (i.e., through complementary base pairing), can be used to specifically localize the sequence controlled polymer to a desired location (e.g., a substrate or surface). In some embodiments, the specific location is specifically selected or otherwise activated for data retrieval or manipulation.

Thus, while the identifier sequence can be used as a priming site for identification, amplification, replication, etc., it can also be used to physically manipulate the sequence such as to bring it to a defined location on a chip or into a defined well, and described herein are methods to, for example, address polymer (e.g., DNA) sequences to capture them to specific positions for applications such as triggered synthesis and sequencing for polymers containing that address sequence.

Additionally or alternatively, the sequence of the identifier can be used to catalog or otherwise identify or characterize the information stored by the sequence controlled polymer associated therewith. Thus, in some embodiments, the sequence of the address or barcode also provides identifying information characteristic of the sequence controlled polymer.

In some embodiments, the identifier sequence can be cleaved from the sequence controlled polymer using an enzyme such as nuclease (e.g., DNA endonuclease). In a particular embodiments, the nuclease is DNase. In some embodiments, the cleavage is sequence specific. Thus in some embodiments, the identifier further includes a site for cleavage by an endonuclease (e.g., a restriction site). In some embodiments, the sequence of the sequence controlled polymer is not disrupted or interrupted by cleavage of the identifier.

In some embodiments, the identifier can be replaced or substituted.

It will be appreciated the disclosed strategies are modular in nature, and where not mutually exclusive, can be used in any combination with other storage and retrieval compositions and methods disclosed herein and elsewhere. Thus, in some embodiments, two or more of the disclosed strategies are used in combination alone and/or one or more of the disclosed strategies are used in combination with one or more known storage or retrieval strategies.

III. Compositions, Methods, and Strategies of Storage and Retrieval

A. Physical Localization and Selective Retrieval

For some applications, sequence controlled polymers need to be spatially separated or segregated to populations and/or maintained in different locations on, for example, a silica chip or within a microwell, or on a DNA origami nanostructure, or on a bead. To achieve this result a sequence can be used to address a location on a chip or bead for archival at a location on a chip. The sequence can be at the 5' end, 3' end, internally, or any combination thereof of the sequence controlled polymer.

One of these strategies is in the synthesis and sequencing of sequence controlled polymer (e.g., DNA or RNA) on microprocessor fabricated chips using nanopores or sequencing by synthesis using a polymerase at defined activatable locations. These locations are triggered essentially the same as a switch on the processor, but in the case of semiconductor connections enables the sequencing of a polymer through a nanopore.

By non-limiting example, a sequence of, for example, 20 nt can be used to attach to a chip that has synthesized in a specific location the reverse complement of the 20 nt. This sequence can be used as an address that can bring down or attach the memory-containing sequence controlled polymer with the 20 nt overhang to the chip or other surface such as a well or bead.

When that surface is then also co-localized with a nanopore sequencing or polymerase sequencing setup as known in the art, the sequence controlled polymer residing in the specific location could be triggered for sequencing when access is needed. In this way, the sequence of the specifically addressed sequence control polymer could then be retrieved while leaving nearby address locations untouched. The sequence could then be reconstructed to retrieve the information. As discussed above, a variety of identifier sequence designs are contemplated, and can be used in this method, provided that the principles of specific localization on the surface, typically via hybridization to a resident oligonucleotide, and access to the sequence controlled polymer by selective sequencing can be achieved. Storage and retrieval using this approach is believed to be feasible up to the limitations of the sequencing technology. Hybridization is typically carried out under condition suitable for hybridization to occur, for example, in the presence of buffer containing salts and/or mild detergents.

The approach is further illustrated in FIG. 1. In nanopore sequencing, a protein nanopore is set in an electrically resistant polymer membrane. An ionic current is passed through the nanopore by setting a voltage across this membrane. The current is changed as the nucleotides of a nucleic acid polymer pass through the pore in different combinations. Measurement of that current makes it possible to identify the sequence of the molecule in question.

Nanopore technology is scalable. A core sensing unit of a nanopore can be set in an arrayed sensor chip and used with an Application-Specific Integrated Circuit (ASIC) that controls and measures the experiments. Each microscaffold can support a membrane and embedded nanopore. Each microscaffold corresponds to its own electrode that is connected to a channel in the sensor array chip. Sensor arrays may be manufactured with any number of channels. Each nanopore channel is controlled and measured individually by the ASIC. This allows for multiple nanopore experiments to be performed in parallel.

FIG. 1 illustrates the addition of an array of DNA oligos for address sequences (i.e., capture probes) arrayed in a grid on a chip (e.g., silicon chip) for specific capture of barcoded/addressed sequences to organize and sort data for archival. The sequence controlled polymer is modified at one end to include an address sequence complementary to a capture probe arrayed on the chip followed by an optional linker followed by a memory/data storage sequence of the sequence controlled polymer. The second end of the sequence controlled polymer can include motor protein, adaptor sequence, and/or other elements to facilitate passage of the sequence controlled polymer through the nanopore. FIG. 1 illustrates how a sequence controlled polymer (e.g., a single-stranded DNA to be sequenced) is tethered to the capture probe via complementary between the address sequences of the capture probe and the sequence controlled polymer. In this way, each sequence controlled polymer is affixed to a specific location on the grid, which is predetermined by the user using the address sequences. The anchored sequence controlled polymer typically remains pliable enough that at least one end can be passed through a nanopore and sequenced.

The capture probe can be attached to the grid by its 3' end or 5' end or both the 3' and 5' end, and the aforementioned elements including the address sequence, linker, memory/data storage sequence, and additional elements of the sequence controlled polymer can be arranged in the 5' to 3' or 3' to 5' direction, provided that the sequence controlled polymer can hybridize to the capture probe via complementary between the address sequences of the capture probe and sequence controlled polymer.

Retrieval of the sequence controlled polymer sequence is rapid in the presence of a nanopore along each grid. Preferably, sequencing is triggered for activity by the electrical stimulation, pH, semi conductance, etc. Each nanopore channel can be controlled and measured individually, so each single sequence controlled polymer can be sequenced on demand. Alternatively, entire grids of sequence controlled polymers, or any desired subset of sequence controlled polymers there between, can be sequenced in parallel.

Any suitable storage scheme can be utilized by the user. Each sequence controlled polymer can include data from the same or different sources. Each nanopore can have a unique capture probe, or a subset of pores can feature the same capture probe. In this way, groups of sequence controlled polymers can be stored and optionally retrieved together based on a shared address sequences.

For example, in a non-limiting example, for illustration purposes only, a chip may contain 500 nanopores, where each subsets of 100 nanopore each features a capture probe with the same unique address sequence (i.e., 5 different capture probe sequences on the chip) on or adjacent thereto. Data for storage from one or more sources (i.e., different books, etc.) is converted to nucleic acid sequences, and sequence controlled polymers are synthesized, each sequence controlled polymer from a single source including the same address sequence that can hybridize with the capture probe of one subset of nanopores. In this illustration, sequence controlled polymers encoding data from up to five different sources can, together or separately, be allowed to hybridize to capture probes on the chip. Because each source shares a unique address, the sequence controlled polymers for each source can be stored in known locations on the grid, even without knowing the sequence of any particular sequence controlled polymer, and in combination with sequence controlled polymers from up to four additional sources. By triggering sequencing of sequence controlled polymers only at grid locations associated with a selected capture probe(s), only the desired data is retrieved on demand.

Additionally or alternatively data from a single or multiple sources can be stored in a specific order by driving localization of each sequence controlled polymer using unique capture sequences. In this way, a grid with 500 nanopores may also have 500 different unique capture sequences that can be sequenced in order, to facilitate the reassembly of the stored data.

The relationship between the grid locations and sequence controlled polymer stored there can be organized using any suitable means, for example, a table or spreadsheet with identifiers that link the grid locations, to capture probe sequences, to sequence controlled polymer source, etc., or locations can be dictated by computer instructions such that the data to be retrieved is stored in a register connecting the address to the instruction.

Suitable materials that can be modified for use with the disclosed devices and techniques are known in the art, and can include, for example, solid-state nanopores and arrays thereof such as those described in Yuan, et al., "Solid-State Nanopore," *Nanoscale Res Lett.* 2018; 13: 56. The sequencing can be triggered by, for example, electric field or signal, pH, semi conductance, etc. or other means that are known in the art.

Figure 2:
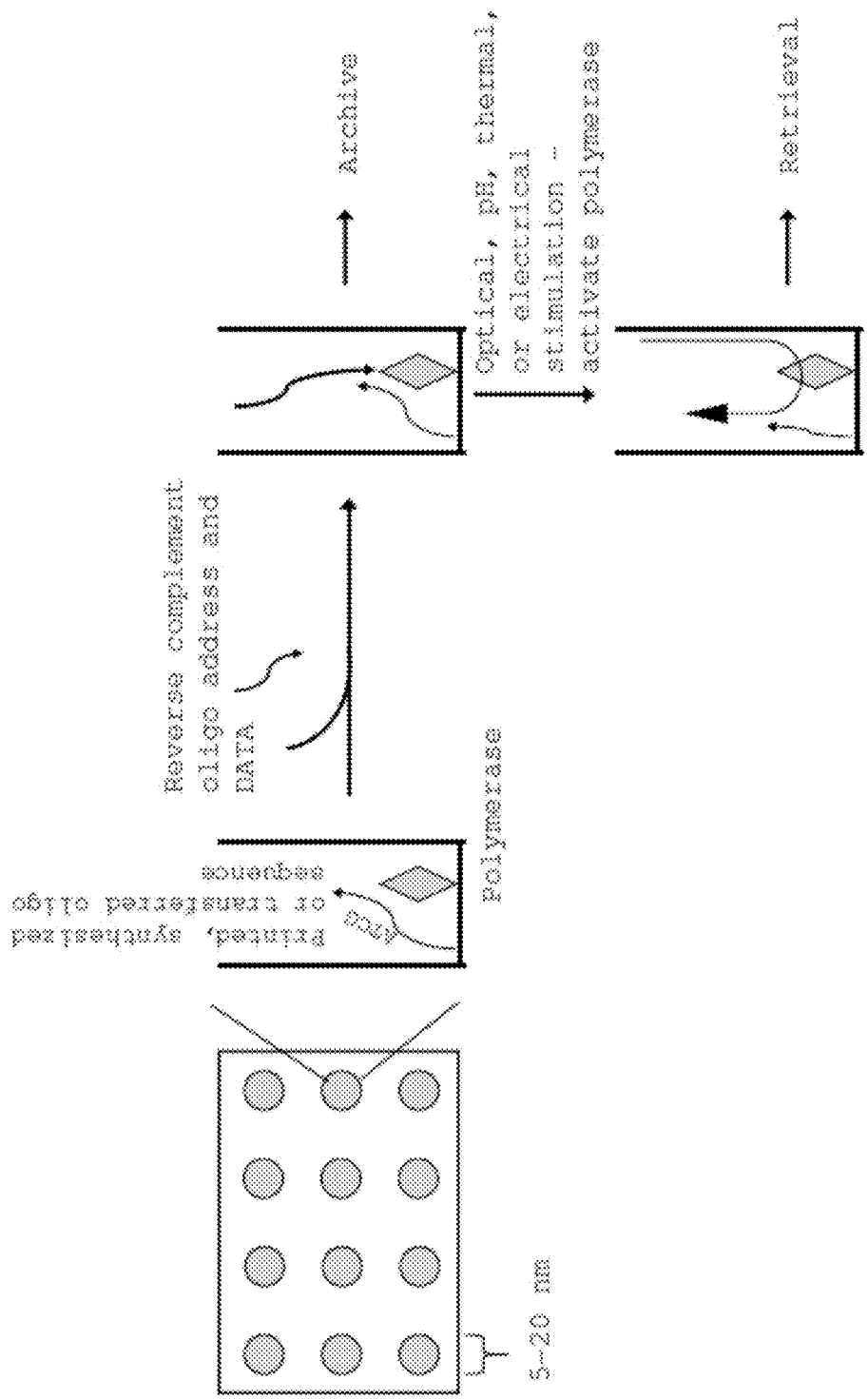
FIG. 2 is a flow diagram illustrating spatial addressing for sequencing by synthesis. A schematic shows sequencing in e.g., microwells with the address loaded based upon complementation to the address synthesized in the well.
Figure 3A:
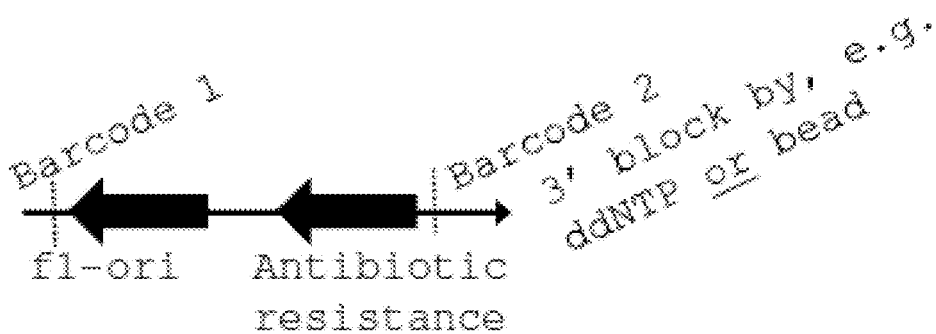
FIGS. 3A-3D illustrate ligation addressing and high-throughput cloning into phage (e.g., a phage library). A universal flanking sequence is complementary to a sequence containing a phage origin of replication, and restriction free cloning is used to ligate the barcoded strand to form a replication module containing the digital information.
Figure 3B:
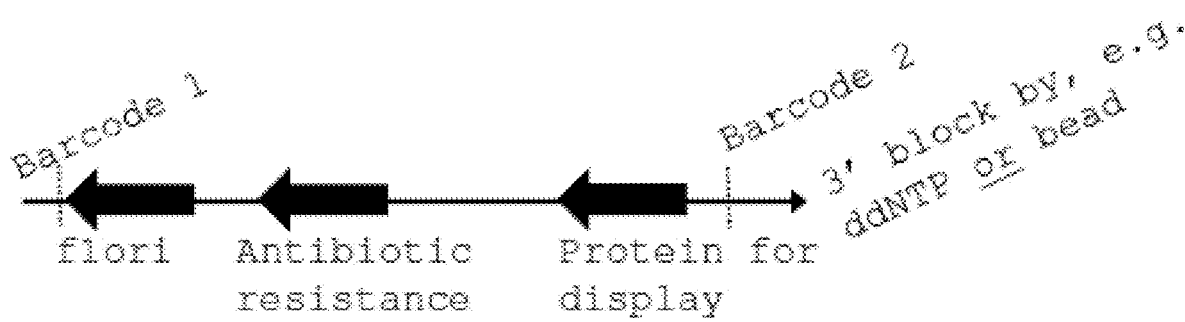
Figure 3C:
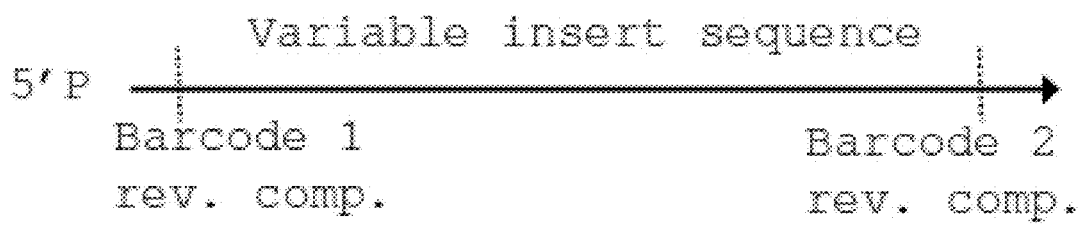
Figure 3D:
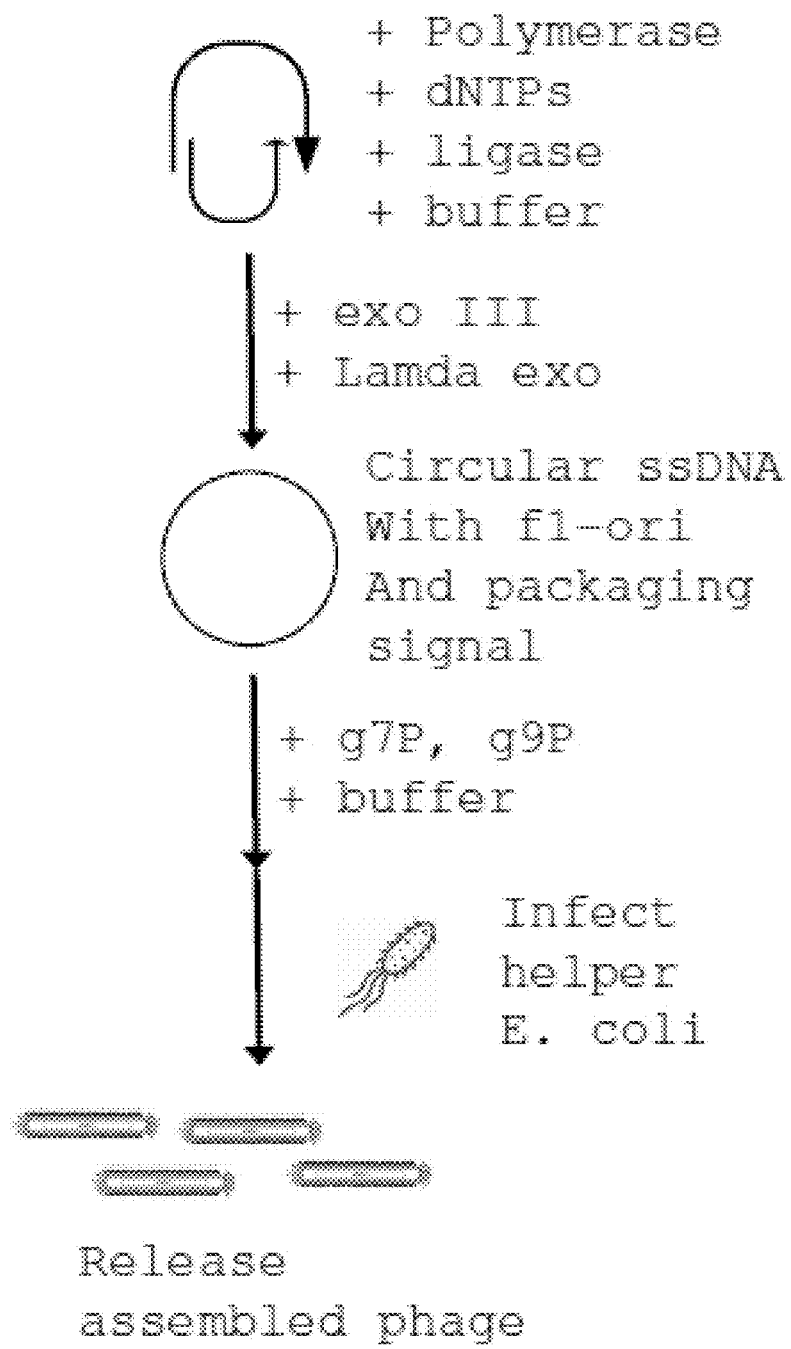

A variation of these materials and techniques designed to accommodate alternatives to nanopore sequencing including, but not limited to, Sanger sequencing, synthesis-by-sequencing technology (e.g., by Illumina), and other sequencing tools and techniques including, but not limited to, single-molecule real-time sequencing (SMRT) (e.g., by PacBio), and hybrid sequencing techniques such as those discussed in Rhoads and Au, *Genomics, Proteomics and Bioinformatics,* 13(5):278-289 (2015), is illustrated in FIG. 2. For example, a microwell plate can replace the nanopore grid. A capture probe complementary to the sequence controlled polymer is seeded at the base of each well. The sequence controlled polymer is floated over the wells and loaded based on complementarity, generally as discussed above with respect to the nanopore-based devices and techniques.

Polymerase loaded to each well will enable sequencing from e.g., Phi29 polymerase, as it reads out the sequence, which can be converted back to its original data (e.g., digital bitstream data). The wells, and thus the complementary sequences deposited at the bases thereof, can be organized for selective retrieval of bound data, in a similar fashion to the organization applied to the chip as discussed above. In some embodiments, polymerase, dNTPs, buffer, and/or other materials, tools and techniques needed for sequencing are applied to the desired wells only, in a predetermined order, or a combination thereof, such that only a desired subset of wells are sequenced, the wells are sequenced in a particular order to facilitate reassembly of the data, or a combination thereof.

B. Phage-based Storage and Retrieval Systems

Improved compositions and methods of assembly of a phage genome and infection with a synthetic capsid with applications to storing and retrieving data using bacteriophage technology are also provided.

Bacteriophage are viruses that specifically infect bacteria and have been studied for their applications in structure, scaffolding, protective capabilities, and effects on the bacteria they infect for applications in medicine. Examples of filamentous bacteriophage include Ff phages, these infect *Escherichia coli* carrying the F episome, including M13 bacteriophage, f1 phage, and fd phage; and Pf1 phage, which infect *Pseudomonas aeruginosa.*

One widely studied class of phage is filamentous phage such as M13. M13 has a native genome of between 6,000 and 9,000 nucleotides, encoding 11 genes of which 3 are used for replication, 3 are used for assembly (genes 2, 10, and 5), two are tail proteins (genes 3 and 6), two are head proteins (genes 7 and 9) and one is a coat protein (gene 8). Previously, genes 8 and 3 are used for phage display, a strategy to pan for binding interactions wherein the genes are modified on the 5' or 3' ends to generate proteins displayed on the outside of the phage with the proteins displayed on the N-terminus or C-terminus of the coat proteins. These displayed protein tags are associated with the internal DNA, that can be sequenced after binding. This work has been transformative to biology and antibody design.

*Escherichia coli* (*E. coli*) has been previously shown to produce filamentous phage M13 when infected with wild type phage, and wild type phage can be disrupted in the so-called M13KO7 variant where the packaging signal is disrupted. This loss of packaging allowed for the co-production of synthetic phage that were relatively clean, when the synthetic phage genome ("phagemid") contained a standard single strand origin of replication "f1". This f1 origin contains a single-stranded origin to the replisome, but also contains a packaging sequence that allows the phage to assemble.

This helper M13 was further improved in pure production by the removal entirely of the f1 origin from the M13 genome and replacing it with a low-copy origin of replication that restricts the packaging to just the synthetic sequence. This effectively allowed a strain of *E. coli* to produce phage, even without being capable of being infected by wild type phage.

This production strain was shown to be capable of producing synthetic phage that encode digital information, where the synthetic phage was assembled by a variant of extension overlap polymerase chain reaction. In this variant, two fragments of DNA were hybridized as a top and bottom strand that had complementary sequences flanking the two fragments. PCR polymerase was used to extend the fragments and T4 DNA ligase was used to close the residual nick. The DNA was cloned to the helper *E. coli* and produced as phage. See, e.g., U.S. Published Application No. 2019/0142882, which is specifically incorporated by reference herein in its entirety.

The disclosed methods provide further refinements and improvements to the use of bacteriophage in the production and storage of sequence controlled polymers, and other applications such as phage display.

In some embodiments, the methods include one or more of the following steps:

providing a target insert such as sequence controlled polymer or expression construct in the form of a single stranded nucleic acid flanked by barcodes, and forming a phagemid including the single stranded nucleic acid sequence, barcodes, a bacteriophage origin of replication and packaging signal, and optionally without a bacterial origin of replication;

optionally packaging the phagemid into a synthetic bacteriophage head that can infect *E. coli* in vitro, optionally, but preferably, in the absence of contaminating nucleic acid, such as double-stranded DNA; and optionally transfecting or infecting the *E. coli* with naked phagemid, or phagemid packaged in the synthetic bacteriaphage head, respectively.

Typically the *E. coli* includes helper constructs expressed by plasmids or integrated into its genome to facilitate replication of the phagemid, packaging of the phagemid into recombinant bacteriophage, secretion of the phagemid into the media, or a combination thereof.

Downstream steps can include, for example, isolating the bacteriophage, isolating the phagemid from the bacteriophage, and processing of the single stranded nucleic acid sequence, such as sequencing and conversion of the sequence back to the originally data.

Compositions and an exemplary workflow are illustrated in FIGS. 3A-3D and 4A-4C, and discussed in more detail below. These compositions and methods can be used for cloning of digital information encoding sequencing to a biological reactor using viral particles for propagation of information and panning for phage display target sequence, and are advantageously amenable to a high-throughput cloning format.

1. Vector Template and Insert Sequences

The phagmid can be produced using any suitable means, for example, asymmetric PCR (aPCR) of a vector template and single stranded nucleic acid. The single stranded nucleic acid can be any desired nucleic acid sequence. In some embodiment, the nucleic acid is one that includes an insert that encodes data for storage (i.e., a data storage nucleic acid). In some embodiments, the data storage insert lacks an expression cassette. In other embodiments, the insert is an expression cassette, particularly one that can be used in a phage display-related application.

The vector template typically includes a bacteriophage origin of replication and packaging sequence (e.g., f1 origin from the M13 genome) and optionally, but preferably a sequence encoding a selectable marker, flanked by bar code sequences. The single stranded nucleic acid insert sequence (i.e, storing the data or encoding the expression construct) to be cloned is also flanked by barcodes complementary to the vector barcodes (also referred to as a universal adapter sequence, etc., as discussed herein).

In more particular exemplary embodiments, the vector template and single stranded nucleic acid sequence are synthesized with a 5' barcode sequence between, e.g., 6 nt and 60 nt and a 3' barcode sequence between, e.g., 6 nt and 60 nt. The universal adapter sequences can be, for example, all of the same sequence or can be of several different sequences that are similar, or can be several different sequences that are orthogonal and designed not to interact at temperatures above 36° C.

Separately, a universal origin of replication and antibiotic selection marker and an optional bacteriophage gene (e.g., gene 3 or gene 7 or gene 8 of M13) are cloned or synthesized on a universal vector template with flanking 5' and 3' sequences that are reverse complements of the universal adapter sequences of the desire insert DNA.

The insert DNA and the vector template are typically both single stranded and of opposite direction. In the compositions and workflow illustrated in FIGS. 3A-3D, the top strand encodes the information e.g., for storage and the bottom strand encodes the vector template which presents the encoded information as the reverse complement (e.g., as a "template strand").

The vector template is typically blocked at the 3' prime end, and the vector template and single stranded nucleic acid can be mixed together and allowed to anneal through hybridization of the barcodes. The complementary region between the codes can be, e.g., from 6 nt to 60 nt.

Polymerase can be used to extend the 3' end of the single stranded nucleic acid over the vector template, but is prevented from extending the 3' end of the vector template due to the 3' block. Having the single-stranded nucleic acid encoding the vector template blocked on the 3' end by chemical modification or at synthesis by, for example, di-deoxyribonucleic acid termination ensures that second strand synthesis only occurs across the template completing a single-stranded synthetic miniphage genome sequence.

Thus, the PCR reaction completes the loop to generate a circular single stranded DNA containing the sequence encoding the bacterial origin of replication and packaging sequence as well as the storage sequence. Any suitable polymerase known in the art, preferably one that has low strand displacement, can be used to complete the plasmid vector.

Ligation (phosphorylated primer or use of kinase) or homologous recombination can be used to close the circle. Vector template can linked to a bead or other surface. Having the single-strand vector template attached to a surface or bead allows for reuse of the strand by releasing from the surface or bead or washing from the surface or bead.

In some instances, 5'-phosphorylated insert sequence is used by, for example, generating the insert sequence from a 5'-phosphorylated initial universal adapter sequence primer, or addition of a 5'-phosphate by polynucleotide kinase, recombinant or natural. In some instances, the 5' phosphorylated insert is ligated to close the circle with the phosphorylated end, such as by, for example, incubation with T4 ligase following standard art-recognized protocols for ligation.

In some embodiments, the ligated, closed circular product is incubated with, for example, either Exonuclease III, Lambda exonuclease, a combination of Exonuclease III and Lambda exonuclease or other combinations of exonucleases known to specifically degrade nicked but not closed strands of DNA, such that the vector template and non-closed-circle inserts are digested or degraded, thus cleaning the closed circular synthetic genome away from any intermediates.

Further purification of this closed purified circular single-stranded DNA such as with ethanol precipitation or column purifications can then be applied for subsequent buffer exchange and purification from residual nucleotides.

Exemplary origins include those from single stranded phage such as f1, fd or M13 which allows the construct to enter a single strand replication mode in which the single stranded construct can be packaged into a virus particle when helper phage, e.g., M13K07, or helper plasmid or other helper constructs is added to or otherwise present in the cell carrying the phagemid. An exemplary origin of replication is the 427 nucleotide f1-origin of replication form a class 1 filamentous bacteriophage. Thus, in some embodiments, the long single-stranded phagemid nucleic acid sequence includes the origin of replication from a class 1 filamentous bacteriophage and one or more naturally or non-naturally occurring nucleic acid sequences of between 1 and 1,000,000 nucleotides in length.

Exemplary antibiotic resistance genes include kanamycin, spectinomycin, streptomycin, ampicillin, carbenicillin, bleomycin, erythromycin, polymyxin b, tetracycline, and chloramphenicol. In some embodiments, the long single-stranded nucleic acid scaffold sequence includes a selection marker. An exemplary is the 1,249-nt ampicillin resistance cistron.

In some embodiments, the target single stranded nucleic acid sequence is cloned directly to the bacteriophage origin with a selection marker. In other embodiments, the target sequence is cloned directly to the origin without a selection marker. For example, the absence of a selection marker can further reduce sequence requirements and completely unlink the phagemid from biological sequences. Further, single stranded nucleic acid production directly from bacteria allows for the cloning and scaling of information encoded in bacteria to be extruded to surrounding media for subsequent purification or processing.

The disclosed constructs can, but need not, and preferably do not, contain a plasmid origin of replication for replication of the plasmid in the host organism (e.g., bacteria). Exemplary origins of replication of plasmids include ColE1, pMB1, pUC, pBR322, R6K, p15A, and pSC101. Thus, a bacterial origin of replication may be present or absent from the disclosed constructs.

2. Introduction into a Host Cell

Once the closed circular single-stranded DNA (cssDNA) has been released from the template, and after optional and preferential buffer exchange or purification from the ligation and purification buffers, it can then be transformed into *Escherichia coli* (*E. coli*) that has been or will be transformed with a helper phage or helper plasmid system encoding the genes of, for example, M13.

The 'helper' phage infects the bacterial host by first attaching to the host cell's pilus and then, after attachment, transporting the phage genome into the cytoplasm of the host cell. Inside the cell, the phage genome triggers production of single stranded phagemid DNA in the cytoplasm. This phagemid DNA is then packaged into phage particles. Exemplary "helper" phages are VCSM13, M13KO7, R408, M13cp, hyperphage, R408d3, and KM13. Exemplary bacterial hosts include *Escherichia coli* strains such as ER2738, TG1, SS320 (or MC1061 F' cells). An exemplary bacterial strain is an *Escherichia coli* bacterial "helper strain," such as the strain M13cp.

In a helper plasmid system, the M13 genes can be moved to a double-stranded, low-copy number helper plasmid that is paired with a phagemid that contains a single-stranded origin of replication such as those described herein, that allows for synthesis and packaging of phagemid's ssDNA (Pasqualini, et al. Nature, 380, 364-366 (1996); Winter, et al., Annu Rev Immunol, 12, 433-455 (1994)).

The helper plasmid typically includes the genes of the corresponding phage. In some embodiments, the helper plasmid lacks the phage packaging gene and/or packaging signal. In some embodiments, the microorganism includes the genome of the M13 bacteriophage, or a mutant or variant of the genome of the M13 bacteriophage.

The helper system may include every gene, or may have single or double deletions of genes, for example, having a deleted gene 3 or gene 7, or both gene 3 and gene 7 deleted, which may alternatively be encoded by the phagemid construct.

In some embodiments, the helper plasmid system is improved by entirely removing the f1-origin and packaging signal from a helper plasmid under a chloramphenicol selection marker (*E. coli* strain M13cp) (Chasteen, L., et al. Nucleic Acids Res, 34, e145 (2006)). This strain produces all 10 M13 phage proteins, but the plasmid does not get packaged into the phage particle because the helper plasmid sequence does not contain the packaging signal and is not single-stranded. Cloning into this strain thus allows for the production of pure ssDNA without the requirement of a dsDNA origin, and removes the dsDNA impurities from the produced phage.

Microorganisms that produce pure single stranded nucleic acid of a user-defined length and sequence, typically for data storage, area also provided. The microorganisms typically include a recombinant phagemid, such as those described above; and optionally a double stranded nucleic acid helper plasmid. The host cell can include a lipopolysaccharide pathway. In some embodiments, the lipopolysaccharide pathway is disrupted. An example of such a host cell is ClearColi by Lucigen, but modified with the phage assembly pathway within the host cell to allow for phage production and additionally and preferentially modified to be a host strain for M13 infection with introduction of the F-pili.

Transformation of the synthetic miniphage genome can be through any means known to the art including chemical transformation, heat shock, electroporation, sonication, detergent based methods, ion based methods.

In an alternative to standard methods of transformation, phage coat proteins themselves may be used for in vitro assembly of an infection-positive cssDNA. To do so, some subset of phage proteins from the M13 or any filamentous phage, or any lambda phage for example can be used for binding to the DNA for insertion into the *E. coli*. This procedure does not require that the cells be electrocompetent, saving this step which can be damaging to cells. This can be a transfection-independent method of introducing the phagemid into bacteria.

As an example, gene 7 and gene 9 of the M13 phage genome can be expressed and purified using methods known in the art. For example, gene 7 and gene 9 can be expressed with an N-terminal or C-terminal histidine tag containing, e.g., 5-10 histidine repeats at one or both ends of the proteins, and purified by a nickel column. Alternatively, wild-type proteins can be purified by ion exchange and size exclusion chromatography.

The expressed, purified proteins can be mixed under suitable conditions, for example, including various buffers (Tris, HEPES, MOPS, etc.) and salts (KCl, K-acetate, K-glutamate, NaCl, Na-acetate, $MgCl2$, Mg-(Glu)2, Mg(acetate) 2), and/or detergents (Triton X-100 for example) and annealed in the presence of the synthetic miniphage genome.

Incubation of this protein-nucleic acid complex (e.g., a synthetic phage head) with *E. coli* displaying the f-pili (e.g. strain SS320) and carrying helper genes from the M13 genome can be used to test the assembly of the phage head and confirm the components needed to infect the *E. coli*. More particularly, in some embodiments, f-pili of the *E. coli* has been modified to interact specifically with compatible phage but not with wild type or native phage (also discussed in more detail below). Presence of fully assembled phage will be the readout for active transformation formulations.

This synthetic assembly of the infective phage head, with the capability to infect *E. coli* and able to interact with the packaging signal of the synthesized closed circular DNA will allow for a carrier system to infect *E. coli* with a broad range of DNAs using a single-high-throughput and scalable workflow. Introduction into *E. coli* of the cssDNA for subsequent packaging by the helper phage system will allow export of clean synthetic miniphage that can be used downstream for DNA data storage or for biopanning for biological interactions, or other use cases where cssDNA is enabling such as with CRISPR based editing (see, e.g., WO 2020/051507).

3. Storage and Retrieval

The sequence controlled polymers, most typically as a circular single stranded nucleic acid, preferably composed of DNA, can be stored at any step of the process, including, for example, as a phagemid (circle single stranded DNA (cssDNA)), associated with synthetic phage head, as a fully assembled phage, or resident in transformed or infected bacteria.

Phage or phagemid can be harvested or exported to the media from cultured bacteria, and captured for downstream processing.

For example, from production, phage can be purified in stabilized phage coat protected from and purified on filter paper or spun down into a pellet, or attached to a bead composed of minerals, or modified, such as on a modified silica bead. The phage can then be dried to the filter paper or kept in pellet form in a tube.

The phage can be bound to a surface, for example, a silica bead.

Additionally, or alternatively, phage can be further protected by the addition of a further polymer or mineral layer such as a second surrounding layer of silica, or a layer of alginate, or calcium, or polymer such as agarose, acrylamide, polyethylene glycol, or other polymers known in the art. The bead can then be modified with additional address sequences to identify the phage contained in the encapsulated bead.

Additionally or alternatively, the phage head can be functionalized with an oligonucleotide with the same or a different barcode from the one incorporated into the cssDNA sequence. The barcode can be used to hybridize the phage to a storage means, for example a surface or bead, to a label or otherwise catalog the phage (and thus its cssDNA), or a combination thereof.

Figure 5:
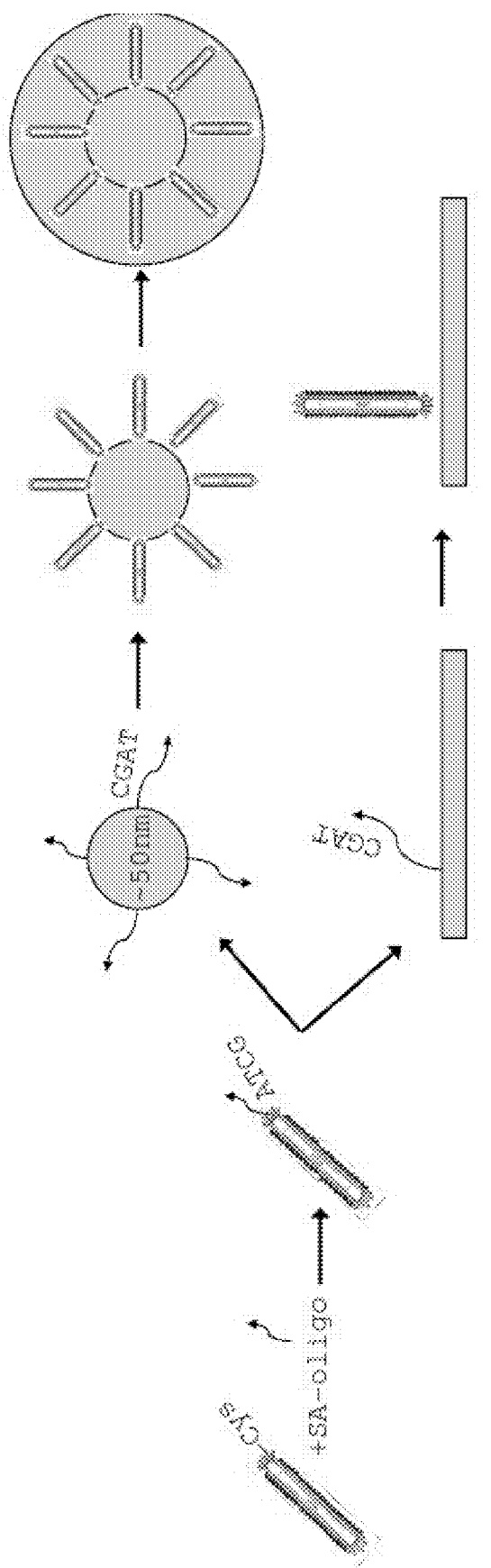
FIG. 5 is a flow diagram illustrating phage-based addressing for self-guided localization on a grid or bead. A schematic of phage with coat protein modified for the addressing of phage to hybridize to a specific location on a 3D bead or on a 2D surface is shown. Address guides can be achieved by reverse complementarity of the sequence.

An exemplary workflow is illustrated in FIG. 5. Phage gene 3 or gene 7 or gene 9 or gene 8 proteins are genetically or chemically modified with a cysteine or a lysine group allowing for chemical attachment of short oligonucleotides to each of the groups of phage. The subsequent interaction between the phage and the surface or bead enables self localization to the particular bead or surface. The surface of the bead can then be protected by mineralization or coated or otherwise protected with e.g., calcium, PEG, silica, or other polymers.

For example, in particular embodiments, a synthetic phage produced as described herein can additionally encode in the vector template a gene 7 or gene 9 or gene 3 or gene 8 that has on its N-terminus or C-terminus a peptide extension including a lysine or cysteine. In other embodiments, lysine or cysteine or peptide containing the same is inserted into the capsid sequence. The lysine or cysteine can be modified with azido or sulfur chemistry (e.g., "click" chemistry) to attach a DNA address sequence (i.e., barcode sequence) to the phage. This sequence can serve as an attachment site to the reverse complement oligo attached to a surface location or a bead. The attachment would then be sortable based on the bound fraction.

Such methods can allow for isolation and/or, pooled or aggregated storage of data housed with the same or different barcodes as selected by the user and determined by mating the barcode sequences between the phage display and storage surface.

In some embodiments, phage heads are chemically or genetically modified to display a ligand. This can be carried out using, for example, traditional phage display methodology. Briefly, a gene encoding a protein of interest is inserted into a phage coat protein gene, causing the phage to "display" the fusion protein including the ligand as part of its coat. Typically, this encoded protein or portion of protein is within the gene 3 or gene 8 of the phage genome, and is included in the phagemid genome to allow for association of the produced fusion protein with the packaged phagemid genome. The bacteria paired with this approach may lack gene 3 and/or gene 8 (e.g., helper plasmids or bacterial genome may not encode genes 3 and/or 8), so the only genes 3 and/or 8 expressed are fused to the display protein. Purified fusion protein can be combined with phagemid in vitro, or the fusion protein can be encoded and expressed by the phagemid or by helper plasmids and form part of the phage during in vivo assembly, as introduced above.

These ligand-displaying phages can be combined and stored in any suitable means, including those mentioned above. In some embodiments, pools of phage displaying different display ligands can be pooled or otherwise stored together. The pool of phage can be mixed with a bacteria strain expressing a receptor for a particular phage fusion protein ligand, allowing for selective amplification and downstream processing of the phage and decoding of the data stored therein. In some embodiments, the bacteria is homogenous for expression of the desired bait receptor. In particularly preferred embodiments, the ligand is an antigen binding protein such as an antibody or fragment or fusion protein related thereto, and the receptor is the antigen for the antigen binding protein. In other particularly preferred embodiments, the ligand is an antigen for an antigen binding protein and the receptor is the antibody or fragment or fusion protein related thereto.

In some embodiments, the capture of the phage from the ligand may only increase the number of phage near the infection point and would statistically increase the infection of the chosen phage.

Preferably, ligand-receptor binding or other interaction between the phage and bacteria triggers the uptake into the phage into the bacteria. Thus, preferably, the infection is selective, and reduces non-selective phage (e.g., incapable of the ligand-receptor binding or other interaction) from infecting the bacteria. In preferred embodiments, the phage ligand binds or otherwise interacts with a receptor displayed on the pili of the capture *E. coli*. Thus, in some embodiments, the receptor is expressed as a fusion protein fused with a pili protein.

Bacterial pili proteins are known in the art. For example, *E. coli* Type 1 pili are peritrichously expressed filamentous surface structures ranging from a few fractions of a micron to greater than 3 microns in length. These organelles are composite structures having a 7-nm-thick right-handed helical rod made up of repeating FimA subunits joined to a 3-nm-thick distal tip fibrillum containing two adaptor proteins, FimG and FimF, and the adhesin, FimH. The expression and assembly of type 1 pili utilize at least eight genes that are present in the type 1 pilus gene cluster (Shilling, et al., *The Journal of Infectious Diseases*, Volume 183, Issue Supplement_1, March 2001, Pages S36-S40, doi:10.1086/318855). Such proteins can be targeted for fusion with a receptor protein using standard cloning techniques. The fusion construct can be, for example, expressed extrachromosomally (e.g., from a plasmid) or integrated in the bacteria's genome.

Figure 6:
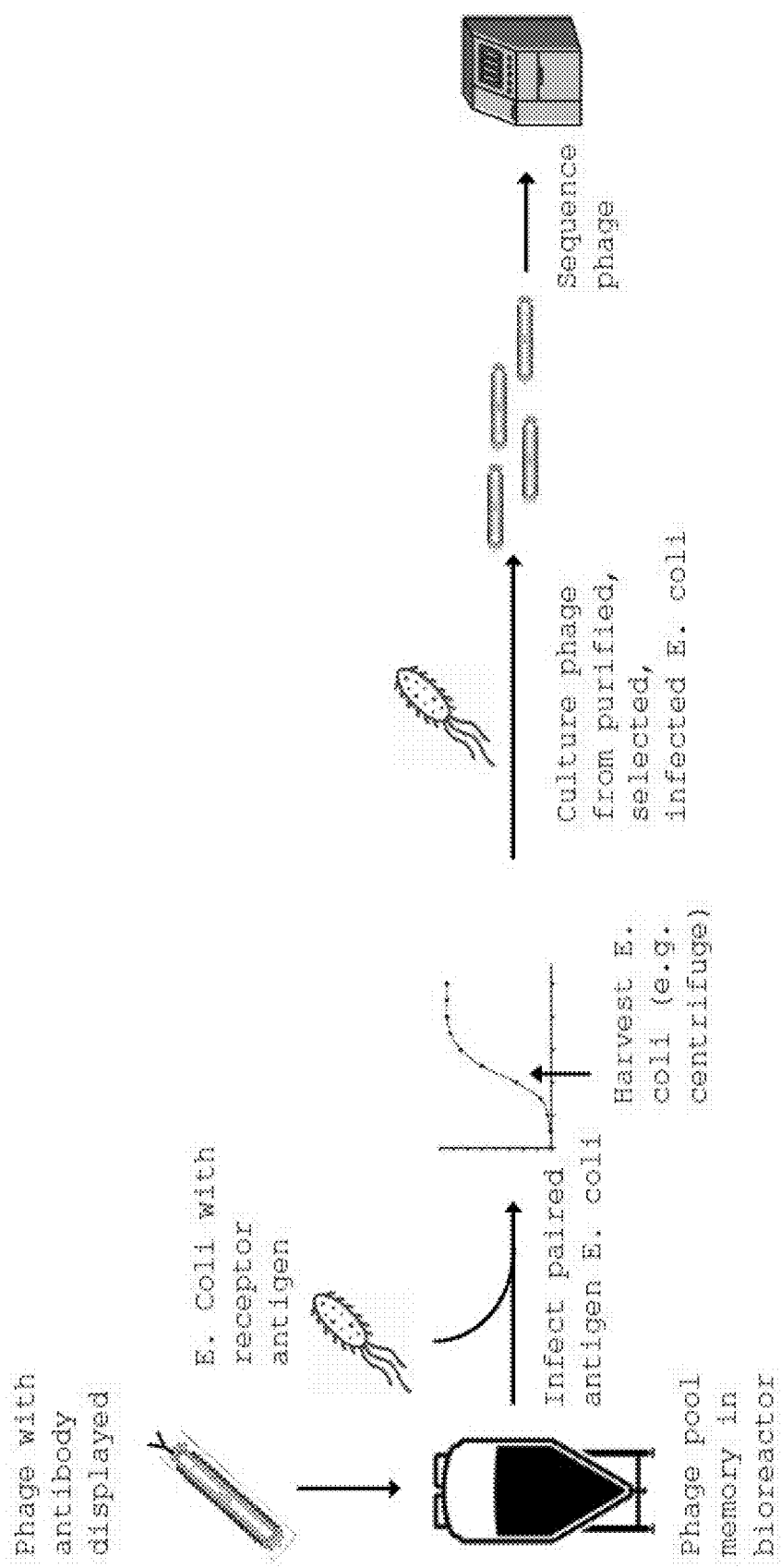
FIG. 6 is a flow diagram illustrating a phage-based approach to controlled infection and amplification in engineered *Escherichia coli*. Schematic representation of a receptor interaction to guide specific infections is shown.

An exemplary workflow is shown in FIG. 6. The figure illustrates that display of antibodies and antigens are one method of binding specific phage to a specialized *E. coli* for probing a bioreactor containing a digital database of information. The subsequent infection of the *E. coli* allows one to harvest and grow the *E. coli* to produce the desired information. Sequencing of the phage that infected the *E. coli* allows reconstruction of the information.

4. Additional and Alternative Embodiments

It will be appreciated that the foregoing compositions and methods have applications beyond data storage, and thus, such methods, which may include cloning, expression, infection, and/or selectively recovering specific phage using bacteria as bait are also provided for other fields including, for example, phage display and other screening based methodologies, for example, as reviewed in Ledsgaard, et al., "Basics of Antibody Phage Display Technology," *Toxins*, 10(236), 15 pages (2018), which is specifically incorporated by reference herein in its entirety.

Figure 4A:
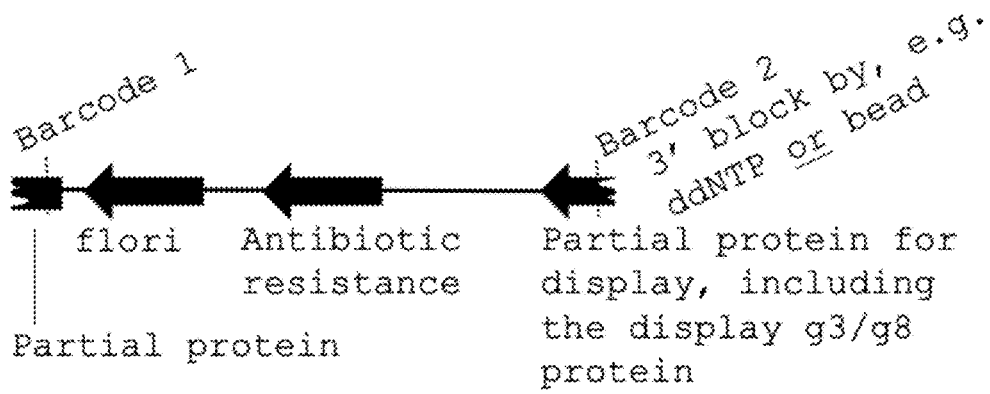
FIGS. 4A-4C illustrate ligation and high-throughput cloning into phage of a variable gene insert and an exemplary workflow of phage production followed by panning and sequencing from a phage library, with cycles of panning, infection, and sequencing selecting out those populations enriched in the panning process.
Figure 4B:
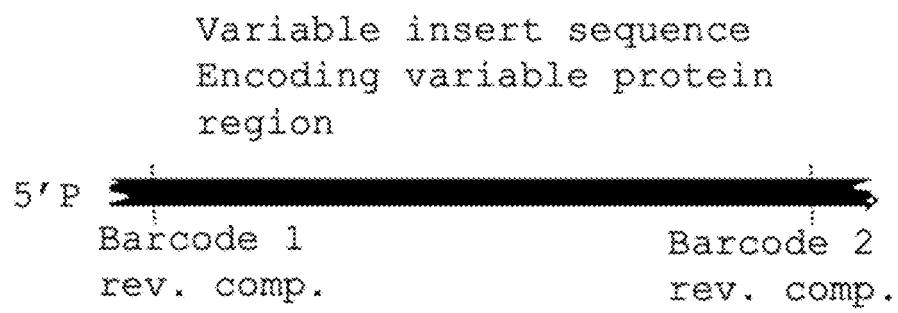
Figure 4C:
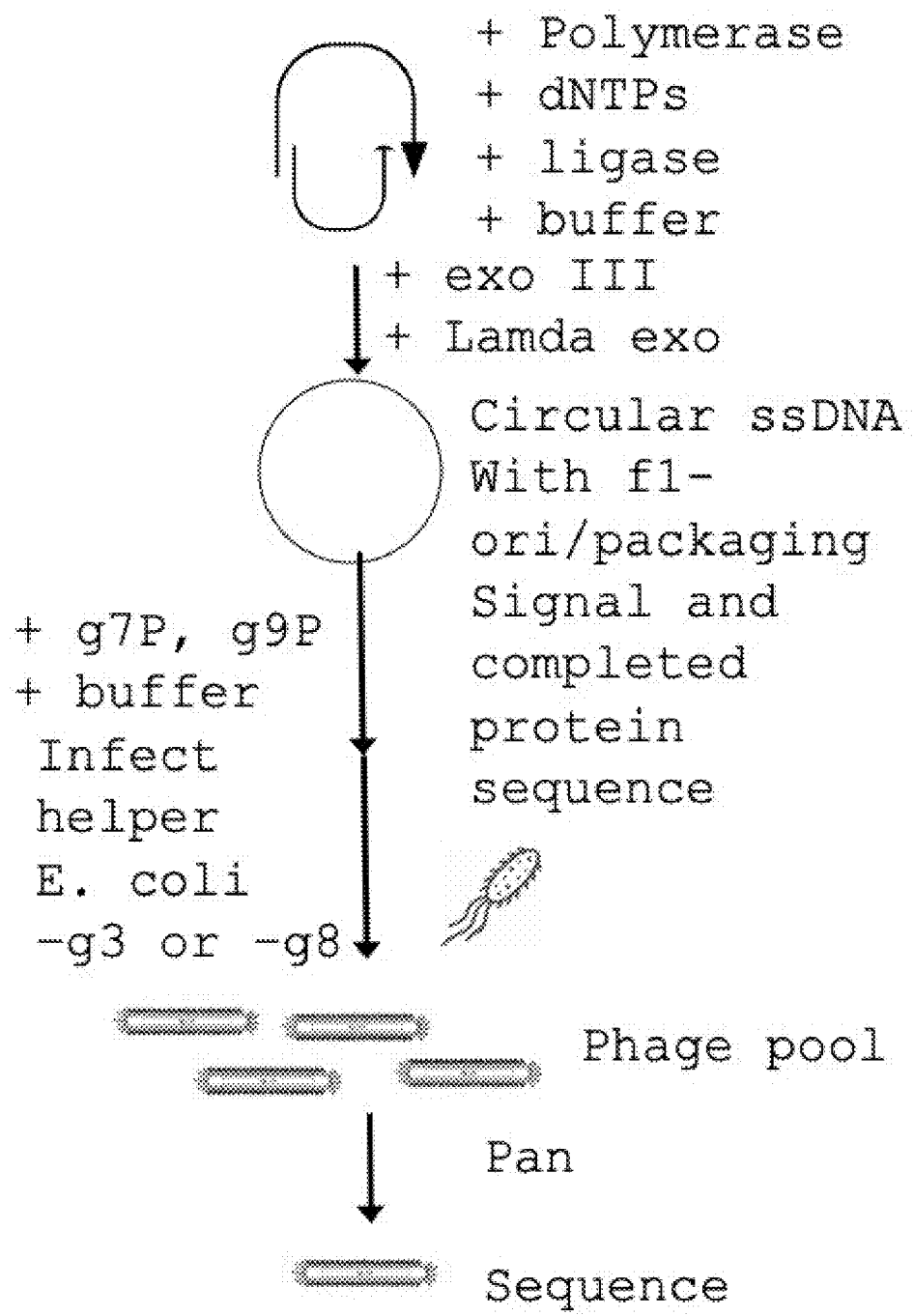

For example, in some embodiments, the insert is, or includes, an expression construct or cassette encoding, for example, a gene or other open reading frame. In some embodiments, the expression construct or cassette can encode an antigen binding protein such as an antibody or antibody fragment or antigen binding fusion protein such as an scFv. The epitope binding region can be variable for high-throughput cloning for use in phage display. In these embodiments, the vector template may include the f1 origin and packaging signal, the optional selection cassette, and the g3 or g8 with the displayed antibody fragment sequence as in phage display. The variable domain can be completed by synthesis of variable sequence oligonucleotides with the barcode universal adapters being the static sequence of the antibody fragment. An Exemplary vector template, insert construct, and work flow are illustrated in FIGS. 4A-4C. Other elements of the methods and would be applicable as described for data storage inserts. For example, the antibody or antigen binding fragment expressed as fusion construct can be selected by binding to an *E. coli* expressing the target antigen of the displayed antigen binding protein.

It will be appreciated that other elements, steps, etc. discussed above with respect to data storage may also be incorporated in these alternative embodiments directed to phage display and other fields.

IV. Tools, Techniques, and Kits

The disclosed methods can utilize any tools and techniques suitable for executed the disclosed strategies. For example, tools and techniques including, but are not limited to, those mentioned herein, including nucleic acid synthesis, nucleic acid linkage and/or printing to surfaces, nucleic acid sequencing technology (e.g., nanopore, Sanger, sequencing by synthesis, SMRT, etc.), PCR, including asymmetric PCR, polymer (e.g., oligonucleotide) synthesis, genetic engineering including, but not limited to, cloning and recombinant bacteriophage engineering and production, and host cell transfection or infection and (e.g., bacterial) culturing.

In some embodiments, the methods include conversion of the data to be stored into a sequence controlled polymer sequence, recovery of the data from the sequence controlled polymer sequence, or a combination thereof.

In some embodiments, the disclosed methods utilize one or more strategies of DNA immobilization, such as those discussed in, Rashid and Yusof, "The strategies of DNA immobilization and hybridization detection mechanism in the construction of electrochemical DNA sensor: A review," Sensing and Bio-Sensing Research Volume 16, Pages 19-31, doi:10.1016/j.sbsr.2017.09.001 (2017), which is specifically incorporated by reference herein in its entirety.

In some embodiments, the disclosed methods utilize electrowetting on a dielectric. Electrowetting (EW) on a dielectric (EWOD) is a variant of the EW phenomenon that is based on dielectric materials. During EWOD processes, a tiny droplet of a conducting liquid is placed on a dielectric layer with insulating and hydrophobic properties. See, e.g., Kim, et al., *J. Mater. Chem. C*, 6:6808-6815 (2018).

Electrowetting on a dielectric is one method for addressing printing of oligos to silica and capturing specific memory blocks to a location with the oligo to ensure capture of the strand. This methodology may be helpful in reducing problems with the kinetics of attachment, reduce the fluid volume and/or amount of library needed, and facilitated loading of limited subsets of addresses, rather than all addresses on a single surface.

Some embodiments utilize materials and methods used in phage display. See, e.g., Ledsgaard, et al., "Basics of Antibody Phage Display Technology," *Toxins*, 10(236), 15 pages (2018), which is specifically incorporated by reference herein in its entirety.

Kits including one or more of the disclosed compositions, optionally in combination with additional materials for facilitate use thereof (e.g., buffers, polymerase, dNPTs, surfaces, etc.), and also provided. Kits may also include containers and/or instructions for use.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A nucleic acid molecule comprising nucleic acid sequences encoding
   (i) an insert,
   (ii) two barcodes,
   (iii) a bacteriophage origin of replication, and
   (iv) a bacteriophage packaging signal
   wherein the barcodes are not part of the insert; and
   wherein the barcodes independently facilitate physical sorting, organization, storage, and/or retrieval, optionally selective retrieval, of the nucleic acid molecule.

2. The nucleic acid molecule of claim 1, wherein the nucleic acid molecule is circular.

3. The nucleic acid molecule of claim 2, wherein the insert is separated from the sequences encoding the bacteriophage origin of replication, bacteriophage packaging signal, selectable marker, or a combination thereof by the barcodes.

4. The nucleic acid molecule of claim 3 further comprising a nucleic acid sequence encoding a selectable marker.

5. The nucleic acid molecule of claim 4, wherein the molecule does not comprise a sequence encoding a bacterial origin of replication.

6. The nucleic acid molecule of claim 5, wherein the nucleic acid molecule is single stranded.

7. The nucleic acid molecule of claim 6, further comprising a nucleic acid sequence encoding between about 1 and 4 bacteriophage capsid proteins, or fusions proteins thereof.

8. The nucleic acid molecule of claim 6, wherein the insert encodes data.

9. The nucleic acid molecule of claim 8, wherein the insert does not encode a gene or other open reading frame.

10. The nucleic acid molecule of claim 9, wherein the data is digital data, optionally bitstream data.

11. The nucleic acid molecule of claim 10, wherein the bacteriophage origin of replication is f1, the selectable marker is an antibiotic resistant gene, the insert sequence encoding data is between about 50 and 50,000 nucleotides in length, and wherein the nucleic acid molecule optionally further comprises a sequence encoding M13 capsid protein(s) or fusion protein(s) thereof.

12. The nucleic acid molecule of claim 6, wherein the insert encodes an expression construct.

13. The nucleic acid molecule of claim 12, wherein the expression construct encodes an antigen binding protein,
optionally wherein the antigen binding protein is an antibody or fragment or fusion protein thereof.

14. The nucleic acid molecule of claim 1, wherein the two barcode sequences are the same.

15. The nucleic acid molecule of claim 1, further comprising one or more bacteriophage capsid proteins associated therewith,
optionally wherein the bacteriophage capsid proteins are g7 and g9 from M13, and/or
optionally wherein the nucleic acid molecule is packaged into a synthetic bacteriophage head formed from the bacteriophage capsid proteins.

16. A method of making the nucleic acid molecule of claim 1, comprising incubating a single stranded vector template comprising the reverse complementary sequence to the two barcodes, the bacteriophage origin of replication, and the bacteriophage packaging signal with a single stranded precursor nucleic acid comprising the nucleic acid sequences encoding the insert and the two barcodes under conditions that allow the vector template to hybridize at the barcodes sequences, and polymerase to extend the single stranded precursor nucleic acid over the vector template to form the nucleic acid molecule.

17. The method of claim 16, further comprising ligating the nucleic acid molecule to form a circular nucleic acid molecule.

18. The method of claim 17, wherein the 3' end of the vector template is blocked to prevent extension of the vector template by the polymerase and leading to a circular single stranded nucleic acid molecule.

19. The method of claim 18, wherein the vector template is linked to a surface.

20. The method of claim 17, wherein the circular nucleic acid molecule is digested with a nick-specific exonuclease(s) to digest residual vector template and non-closed circular single stranded nucleic acid molecules,
optionally wherein the exonuclease(s) is Exonuclease III, Lambda exonuclease, or a combination thereof.

21. The method of claim 18, further comprising incubating the circular single stranded nucleic acid molecule with one or more bacteriophage capsid proteins,
optionally wherein the bacteriophage capsid proteins are g7 and g9 from M13,
wherein the nucleic acid molecule is packaged into a synthetic bacteriophage head formed from the bacteriophage capsid proteins.

22. A method of introducing a nucleic acid into cells, comprising incubating the bacteriophage capsid protein-associated nucleic acid molecule of claim 15 with F-pili *E. coli*.

23. A method of storing a data storage nucleic acid molecule comprising selectively linking a bacteriophage to a desired physical location on a surface,
wherein the bacteriophage comprises a genome comprising the nucleic acid molecule of claim 8, and capsid protein linked to a phage barcode;
wherein the surface comprises the reverse complement of the phage barcode at the physical location; and
wherein the bacteriophage and the surface are brought into contact under conditions that the allow the phage barcode to hybridize to the reverse complement on the surface.

24. The method of claim 23, wherein the surface is a bead, a chip, a well, glass slide, or a plate.

25. The nucleic acid molecule of claim 1, wherein the barcodes independently provide localization and/or hybridization information for the nucleic acid molecule.

26. The nucleic acid molecule of claim 1, wherein the nucleic acid molecule encodes a bacteriophage g3 and/or g8 protein.

27. The nucleic acid molecule of claim 26, comprising a nucleic acid sequence encoding an antigen binding domain of an antibody, optionally wherein the antigen binding domain is a single chain variable fragment (scFv).

28. The nucleic acid molecule of claim 1, wherein the barcodes each comprise a sequence encoding a part of a bacteriophage g3 and/or g8 protein.

29. The nucleic acid molecule of claim 26, wherein the barcodes each comprise a sequence encoding a part of the bacteriophage g3 and/or g8 protein.

* * * * *